(12) United States Patent
Nakamura et al.

(10) Patent No.: US 11,720,801 B2
(45) Date of Patent: Aug. 8, 2023

(54) CHEMICAL REACTION NETWORK FOR ESTIMATING CONCENTRATION OF CHEMICAL SPECIES BASED ON AN IDENTIFIED PATTERN OF OUTPUT CHEMICAL SPECIES

(71) Applicant: International Business Machines Corporation, Armonk, NY (US)

(72) Inventors: Eiji Nakamura, Tokyo (JP); Toshiyuki Yamane, Kanagawa (JP); Koji Masuda, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 106 days.

(21) Appl. No.: 17/001,804

(22) Filed: Aug. 25, 2020

(65) Prior Publication Data
US 2022/0064700 A1    Mar. 3, 2022

(51) Int. Cl.
*G06N 3/123* (2023.01)
*C12Q 1/686* (2018.01)

(52) U.S. Cl.
CPC ............. *G06N 3/123* (2013.01); *C12Q 1/686* (2013.01)

(58) Field of Classification Search
None
See application file for complete search history.

(56) References Cited

FOREIGN PATENT DOCUMENTS

| EP | 3188836 A1 | 7/2017 |
| EP | 1583843 B1 | 7/2018 |

OTHER PUBLICATIONS

Stangeland, B. E., and A. S. Foss. "Control of a fixed-bed chemical reactor." Industrial & Engineering Chemistry Fundamentals 9.1 (1970): 38-48.*
Chen, Yuan-Jyue, et al. "Programmable chemical controllers made from DNA." Nature nanotechnology 8.10 (2013): 755-762 with 55 pages of "supplementary information".*
Nakamura et al., "Multi-species consensus network of DNA strand displacement for analog-to-digital conversion for nucleic acid concentration", IBM Research, licensed under Creative Commons License CC-BY, printed Jul. 31, 2020, 15 pages.
DNA Strand Displacement, YouTube, dated Jun. 22, 2016, 2 pages.
Lakin et al., "Visual DSD: a design and analysis tool for DNA strand displacement systems", Microsoft Research, fated Nov. 2011, 3 pages. ittps://www.microsoft.com/en-US/research/publication/ . . . .
Lopez et al., "A molecular multi-gene classifier for disease diagnostics", Articles, Nature Chemistry, vol. 10, Jul. 2018, 11 pages.
Soloveichik et al., "DNA as a universal substrate for chemical kinetics", PNAS, Mar. 23, 2010, vol. 107, No. 12, 6 pages. www.pnas.org/cgi/doi/10.1073/pnas.0909380107.
Islam et al., "RNA Biomarkers: Diagnostic and Prognostic Potentials and Recent Developments of Electrochemical Biosensors", Research Gate, Jun. 2017, RNA Biomarkers, Small Methods, 21 pages.
Chou, "Chemical reaction networks for maximum likelihood estimation of the concentration of signalling molecules", NANOCOM '17, Washington D.C., 2017 ACM, 2 pages.
Chen et al., "Programmable chemical controllers made from DNA", Nature Nanotechnology, Articles, Published Online: Sep. 29, 2013 | DOI: 10.1038/NNANO.2013.189, 8 pages.

* cited by examiner

*Primary Examiner* — G. Steven Vanni
(74) *Attorney, Agent, or Firm* — James L. Olsen

(57) ABSTRACT

A technique for performing a function by utilizing chemical reactions is disclosed. In the technique, solution including an input chemical species having a concentration is provided. A chemical reaction network that includes at least a sequence of chemical reactions starting with the input chemical species to generate a plurality of output chemical species is also prepared. The solution is exposed to the chemical reaction network to present a pattern formed by the plurality of output chemical species depending on the concentration of the input chemical species.

21 Claims, 16 Drawing Sheets

FIG. 2

CHEMICAL REACTION NETWORK FOR ESTIMATING CONCENTRATION OF CHEMICAL SPECIES BASED ON AN IDENTIFIED PATTERN OF OUTPUT CHEMICAL SPECIES

BACKGROUND

The present disclosure, generally, relates to artificial chemical circuits to perform a function, more particularly, to methods and chemical circuit devices for performing a function by utilizing chemical reactions.

Implementing sensing or a computational function into chemical reactions rather than electronic devices itself is one of the emerging approaches. Synthetic biologists have developed a variety of artificial biological circuits, including logic gates, analog circuits, toggle switches, oscillators, signal amplifiers, memory, etc. While the process of the consensus formation has been of practical interest in some research areas such as distributed computing and sensor networks, recently a two-species consensus network using chemical reaction systems of DNA (deoxyribonucleic acid) strand displacement reaction has been proposed (Y. J. Chen, et. al., "Programmable chemical controllers made from DNA", Nature Nanotechnology, 8, 755-762, 2013).

Although some of the aforementioned artificial circuits have been well-established, the list of the biological and/or chemical circuit components still needs to be further extended to realize more complex functions.

Meanwhile, the concentration of the nucleic acid (DNA and RNA (ribonucleic acid)), especially RNA, has meaningful information in the living cells. In the living cells, DNA is transcribed to RNA and RNA is translated to proteins in the sequential process called 'central dogma'. The set of RNAs in one cell or a population of cells is called transcriptome, which recently has attracted attention because of its importance for elucidating cellular dynamics. Many types of the RNA sequence are reported as biomarkers for specific diseases, which potentially enables us to detect certain cell types or diseases by measuring the presence and/or the concentration of the RNA sequence.

Although there are several methods for analyzing nucleic acids, including RT-qPCR method, DNA microarrays, next-generation sequencers and electrochemical devices, these technologies have practical challenges in terms of the cost, the sensitivity and the dynamic range. The concentration, which is an analog signal, is not readily accessible because the quantitative measurement of the concentration of RNA usually requires expensive tools and is time-consuming and labors intensive.

Hence, there is a need for a novel technique capable of classifying a concentration of a chemical species such as nucleic acids into one of classes represented in more accessible forms in a chemical circuit.

SUMMARY

According to an embodiment of the present disclosure, a method for performing a function by utilizing chemical reactions is provided. The method includes providing solution that includes an input chemical species having a concentration. The method also includes preparing a chemical reaction network that includes at least a sequence of chemical reactions starting with the input chemical species to generate a plurality of output chemical species. The method further includes exposing the solution to the chemical reaction network to present a pattern formed by the plurality of output chemical species depending on the concentration of the input chemical species.

The method according to the embodiment of the present disclosure allows for classification of the concentration of the input chemical species into a class represented by the pattern of the plurality of output chemical species, which is a more accessible form than the concentration of the input chemical species itself.

In a preferable embodiment, the function is readout of the concentration of the input chemical species. The method further includes identifying the pattern by detecting at least presence of each of the plurality of output chemical species. The method includes further estimating a concentration range to which the concentration of the input chemical species falls according to the pattern of the output chemical species. Thereby, it enables us to read the concentration of the input chemical species in a more readable form than the concentration of the input chemical species itself, which is generally an analog value of a single variable. Also, the concentration of the input chemical species can be quantified with high robustness and low cost.

In a further preferable embodiment, the pattern indicates a dominant species among the plurality of output chemical species as a result of progress of the chemical reaction network. Thus, the pattern represents a digital signal having '1' (dominant) at a digit corresponding to the dominant species. Such digital signal can be easily detected and then used to compute a level of the concentration of the input chemical species. The readout resolution of the concentration can be improved by increasing the number of output chemical species.

In other preferable embodiment, the estimating includes referring calibration parameters that represents relationship between predetermined patterns and predetermined ranges of the concentration. Thereby, it improves the estimation accuracy.

In yet other preferable embodiment, the function is supply of output chemical species depending on the concentration of the input chemical species. The method includes further supplying at least a part of resultant solution containing the pattern of the output chemical species to a subsequent process. Thereby, the subsequent process can be controlled by the output chemical species that is a function of the concentration of the input chemical species.

In a particular embodiment, the sequence of chemical reactions includes a first set of linked chemical reactions, each of which converts a lower one of the output chemical species into an upper one of the output chemical species, starting from the input chemical species as the lowermost.

In other particular embodiment, the first set of linked chemical reactions includes a set of gate species, each of which is consumed to convert the lower one of the output chemical species into the upper one of the output chemical species. The set of gate species is given at respective initial concentrations that decrease towards the upper side along the first set of linked chemical reactions.

In a particular embodiment, the chemical reaction network includes further a second set of chemical reactions for forming consensus among the plurality of output chemical species generated from the sequence of chemical reactions so as to single out major chemical species.

In further other embodiment, the chemical reaction network includes further a third set of chemical reactions, each of which converts an upper output chemical species into a lower output chemical species with product sides along the sequence of chemical reactions as upper sides.

In a preferable embodiment, the input chemical species is a nucleic acid strand having a representative domain and a toehold domain. The plurality of output chemical species is a plurality of unique nucleic acid strands each having a unique representative domain and a toehold domain. Each reaction in the sequence of chemical reactions includes a cascade of nucleic acid strand displacement reactions. Thereby, the concentration of the nucleic acid strand can be quantified with high robustness and low cost. Since the nucleic acid strand displacement reaction is known for a universal, versatile reaction that can implement arbitrary chemical reaction networks, the chemical reaction network can be designed flexibly. Also, the nucleic acid strand displacement reaction does not require an enzyme and the chemical reaction can proceed by simply exposing the input chemical species to the chemical reaction network. Also, each nucleic acid strand displacement reaction can be implemented using merely nucleic acids.

In a particular embodiment, the cascade of nucleic acid strand displacement reactions includes auxiliary strands with excessive amount so that a bimolecular elementary reaction in the cascade of nucleic acid strand displacement reactions becomes a rate-limiting step.

In a particular embodiment, a rate constant for the cascade of nucleic acid strand displacement reactions is affected by the number of bases and guanine-cytosine content of toehold domains of a nucleic acid strand involved therein. Hence, switching behavior of the chemical reaction network can be tuned by varying the number of bases and/or the guanine-cytosine content of the toehold domain according to requirements from a specific application.

According to other embodiment of the present disclosure, a chemical circuit device for performing a function by utilizing chemical reactions is provided. The chemical circuit device includes an input provision unit configured to provide solution including an input chemical species having a concentration. The chemical circuit device also includes a reactor used to carry out a chemical reaction network, in which the chemical reaction network includes at least a sequence of chemical reactions starting with the input chemical species to generate a plurality of output chemical species. The chemical circuit device further includes a control unit configured to expose the solution to the chemical reaction network to present a pattern formed by the plurality of output chemical species depending on the concentration of the input chemical species.

The chemical circuit device according to the embodiment of the present disclosure allows for classification of the concentration of the input chemical species into a class represented by the pattern of the plurality of output chemical species, which is a more accessible form than the concentration of the input chemical species itself.

In a preferable embodiment, the chemical circuit device includes further a detection unit configured to detect at least presence of each of the plurality of output chemical species to identify the pattern. The chemical circuit device further includes an estimation unit configured to estimate a concentration range to which the concentration of the input chemical species falls according to the pattern of the output chemical species. Thereby, it enables us to read the concentration of the input chemical species in a more readable form than the concentration of the input chemical species itself, which is generally an analog value of a single variable. Also, the concentration of the input chemical species can be quantified with high robustness and a low cost.

In a particular embodiment, the detection unit is based on one technique selected from the group consisting of a polymerase chain reaction (PCR) method, a DNA microarray, a RNA sequencing method, a surface plasmon resonance sensor, a nanopore method, an electrochemical sensor and a colorimetric sensor. Regardless of the technique employed, the requirements on the measurement accuracy can be relaxed to some extent in comparison with direct measurement of the analogue concentration value, thereby resulting in cost reduction.

In a particular embodiment, the chemical circuit device further includes a memory unit for storing calibration parameters that represent relationship between predetermined patterns and predetermined ranges of concentration. The calibration parameters are used to estimate the concentration range to which the concentration of the input chemical species falls. Thereby, it improves the estimation accuracy.

In a particular embodiment, the chemical circuit device further includes an output supply unit configured to supply at least a part of resultant solution containing the pattern of the output chemical species to a subsequent process. Thereby, the subsequent process can be controlled by the output chemical species that is a function of the concentration of the input chemical species.

Additional features and advantages are realized through the techniques of the present disclosure. Other embodiments and aspects of the disclosure are described in detail herein and are considered a part of the claimed disclosure.

BRIEF DESCRIPTION OF THE DRAWINGS

The subject matter, which is regarded as the disclosure, is particularly pointed out and distinctly claimed in the claims at the conclusion of the specification. The foregoing and other features and advantages of the disclosure are apparent from the following detailed description taken in conjunction with the accompanying drawings in which:

FIG. 2 illustrates a schematic of mapping between concentration ranges of the input chemical species and output patterns of the output chemical species in the chemical circuit according to the exemplary embodiment of the present disclosure;

DETAILED DESCRIPTION

Hereinafter, the present disclosure will be described with respect to particular embodiments, but it will be understood by those skilled in the art that the embodiments described below are mentioned only by way of examples and are not intended to limit the scope of the present disclosure.

One or more embodiments according to the present disclosure are directed to methods and chemical circuit devices for performing a function by utilizing chemical reactions: in which solution including an input chemical species having a concentration is provided; a chemical reaction network including at least a sequence of chemical reactions starting with the input chemical species to generate a plurality of output chemical species is prepared; and the solution is exposed to the chemical reaction network to present a pattern formed by the plurality of output chemical species depending on the concentration of the input chemical species.

Hereinafter, first referring to FIGS. 1-9, a chemical circuit and process for classifying a concentration of an input chemical species into a class represented by a pattern of a plurality of output chemical species according to an exemplary embodiment of the present disclosure will be described. Then, referring to FIG. 6, and FIGS. 10-12, a chemical circuit and process for classifying a concentration of an input chemical species into a class represented by a pattern of a plurality of output chemical species according to other exemplary embodiment of the present disclosure will be described. Also, referring to FIG. 13, a chemical circuit device implementing the chemical reaction network and/or the process for classifying the concentration of the input chemical species into a class represented by the pattern of the output chemical species according to an exemplary embodiment of the present disclosure will be described. Finally, with reference to FIGS. 14-16, geometric analysis of the chemical circuit according to the embodiments of the present disclosure will be described from the viewpoint of nonlinear dynamical systems.

Hereinafter, referring to FIG. 1, a schematic 100 of a chemical circuit for classifying a concentration of an input chemical species into a class represented by a pattern of output chemical species according to an exemplary embodiment of the present disclosure is described.

Figure 1:
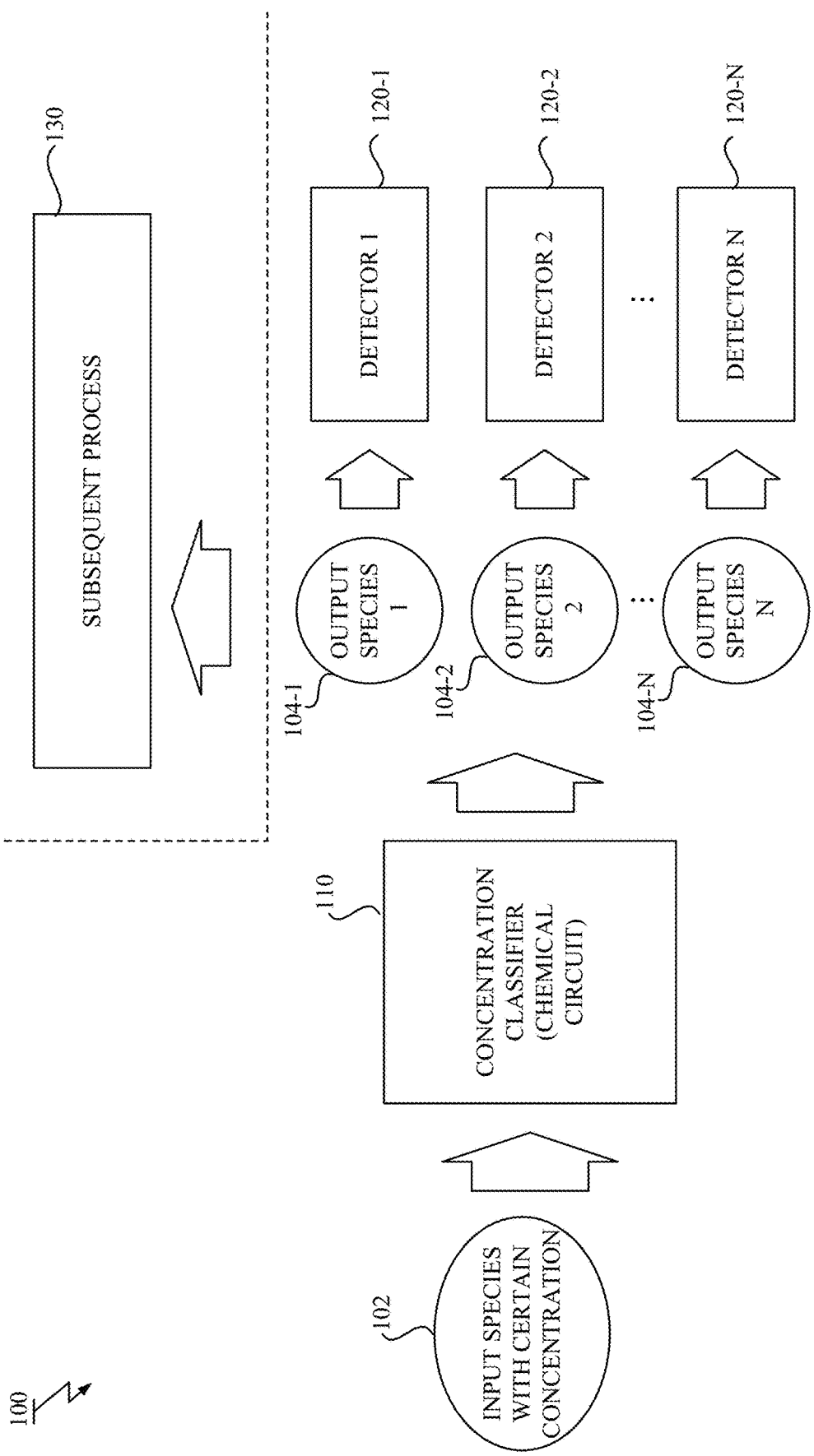
FIG. 1 depicts a schematic of a chemical circuit for classifying a concentration of an input chemical species into a class represented by a pattern of output chemical species according to an exemplary embodiment of the present disclosure.

As shown in FIG. 1, there is a chemical circuit 110 for classifying a concentration of a given input chemical species (the term 'chemical species' may be abbreviated simply as 'species') 102 into a class represented by a pattern of output chemical species 104-1~104-N, where N represents the number of output chemical species involved in the chemical circuit 110.

The chemical circuit 110 involves a chemical reaction network that implements classification functionality (or algorithm) for classifying the concentration of the input chemical species 102 into a class represented by the pattern of the output chemical species 104. Note that the chemical reaction network includes a set of linked chemical reactions and a set of chemical compounds involved in the reactions, thereby forming a network structure. The chemical reaction network will be described in more detail latter.

As a result of progress of the chemical reaction network, more specifically, as steady state or end state of the chemical reaction network, the chemical circuit 110 presents a pattern indicating at least a dominant (or major) species among the plurality of output chemical species 104 depending on the give concentration of the input chemical species 102. The chemical circuit 110 is also referred to as a concentration classifier 110 in a sense that the chemical circuit 110 classifies the concentration of the input chemical species into one of classes (or class intervals), which are represented by different patterns of the output chemical species 104.

The input chemical species 102 and the output chemical species 104 is generally not limited to specific kinds of chemical compounds. Non limiting examples of the chemical species involved in the chemical reaction network may include nucleic acid single and double strands such as DNA (deoxyribonucleic acid) and RNA (ribonucleic acid) single and double strands, synthetic polymers, natural polymers, other organic or inorganic molecules, etc. Although the chemical species involved in the chemical reaction network is not limited, the nucleic acid single strands are preferably used as the input chemical species 102 and the output chemical species 104 since the nucleic acid strand displacement reactions are preferably employed as a building block for forming the chemical reaction network in the concentration classifier 110, as will be described latter.

The molecules of the input chemical species 102 may be provided to the chemical circuit 110 as solution with a certain concentration. The value of the concentration can be defined as a value of a concentration in given solution, which is then supply to a reactor of the concentration classifier 110. Alternatively, the value of the concentration can be defined as a value of a concentration in the whole volume of the solution in the reactor after the supply of the molecules of the input chemical species 102 to the reactor. These concentration values can be converted to each other. The solution may be any appropriate solution. When nucleic acid single strands such as DNA and RNA strands are employed as the input and output chemical species, water or any suitable solution such as Tris-acetate-EDTA (Ethylenediaminetetraacetic acid) buffer solution may be used.

In a particular embodiment, the concentration of the input chemical species 102 carries an analog signal that is meaningful in the given biological and/or chemical system, in a context of DNA computing. In other particular embodiment, the concentration of the input chemical species 102 itself plays a role in relation to the organism and other biological and/or chemical systems. For example, the input chemical species may be a DNA/RNA strand associated with any one of biomarkers and the concentration of the input chemical species 102 indicates a state or condition of the organism or the biological system. For other example, the input chemical species 102 may be a product of a previously performed chemical reaction.

In a particular embodiment, at least presence of the output chemical species 104 carries a signal that is meaningful in the given biological and/or chemical system in a context of DNA computing. The presence or absence of the output chemical species 104 can form a digital signal. The level of presence (or a concentration range) of the output chemical species 104 can form a multi-level signal if the level is distinguishable. Note that term 'multi-level' means having more than two levels (greater than or equal to 3 levels) and does not include binary level. In other particular embodiment, the presence or the concentration range of the output chemical species 104 itself plays a significant role in relation to an organism and other biological and/or chemical systems. For example, the presence or the concentration range of the output chemical species 104 induces state change in the biological system such as gene regulation. For other example, the output chemical species 104 may be used as a reactant or a catalyst of a subsequent chemical reaction.

Hence, the concentration classifier 110 can be regarded as an analog-to-digital (or multi-level) convertor that converts the concentration of the input chemical species 102, which is generally analogue signal, into the pattern of the output chemical species in a form of the digital (binary-level) or multi-level signal.

In FIG. 1, there is further a plurality of detectors 120-1~120~N for detecting a corresponding output chemical species 104-1~104~N. The concentration classifier 110 may provide a readout function of the concentration of the input chemical species 102 by combining the plurality of detectors 120-1~120~N.

Each detector 120 detects at least the presence of the corresponding output chemical species 104. For example, the first detector 120-1 detects at least the presence of the first output chemical species 104-1. The detector 120 distinguishes at least whether the corresponding output chemical species exits in the resultant solution or not. However, the resolution of the detector 120 may not be limited to the binary level. In other embodiment, the detector 120 may distinguish the level of the presence of the corresponding output chemical species to some extent.

FIG. 1 also depicts other use case different from the readout function of the concentration. The concentration classifier 110 may provide a supply function of the output chemical species depending on the concentration of the input chemical species.

As shown in FIG. 1, there is also a subsequent process 130, which uses or consumes the output chemical species generated by the concentration classifier 110 as a reactant or catalyst. The output of the concentration classifier 110 may be transported to the subsequent process 130. The subsequent process 130 may be any one of known chemical and/or biological circuits, including logic gates, analog circuits, toggle switches, oscillators, signal amplifiers, etc., in a context of the DNA computing. Examples of the subsequent process 130 may also include any known biological reactions such as translation of RNA into a protein when the output chemical species is a messenger RNA, for instance.

Figure 2:
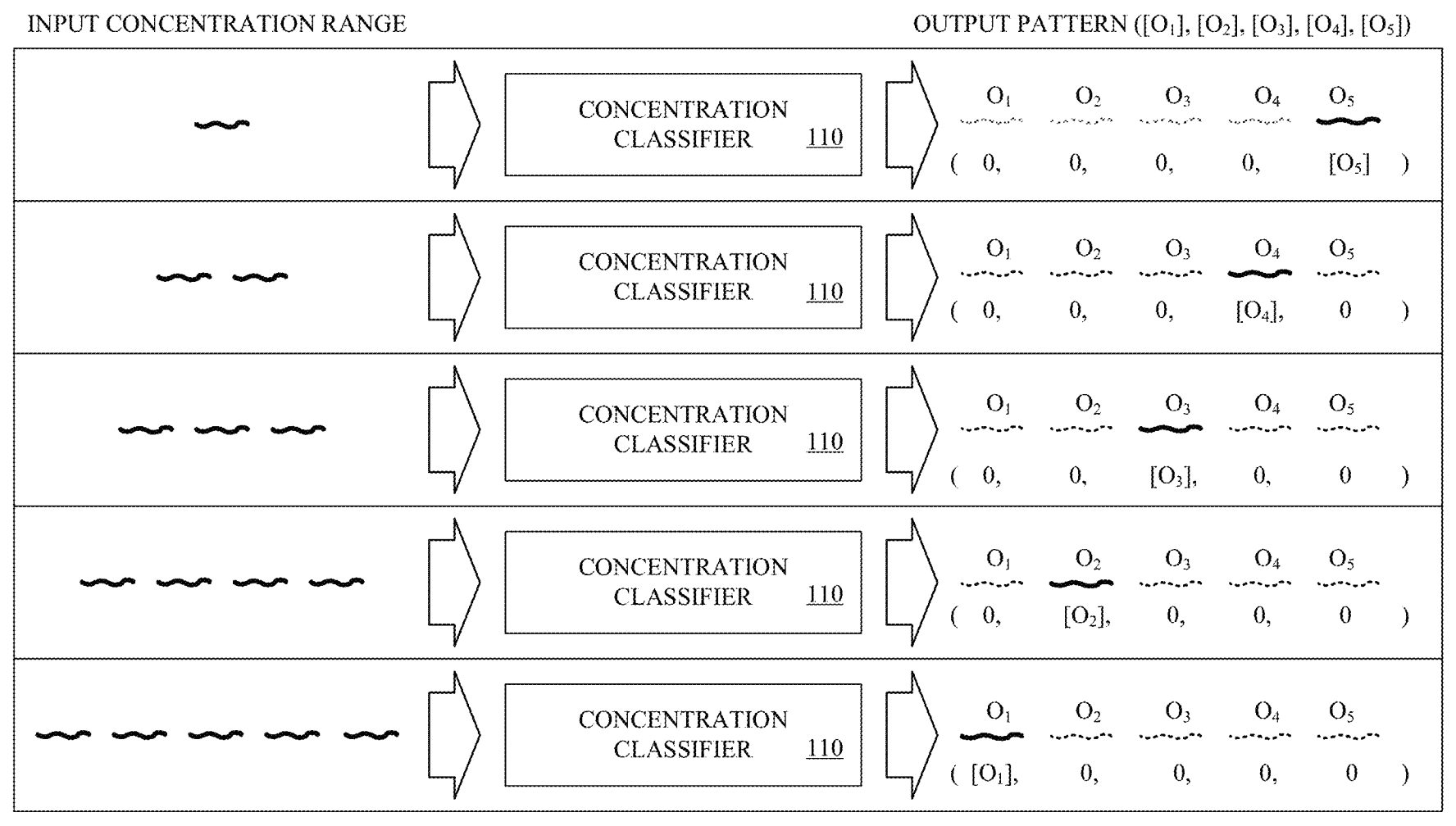

FIG. 2 illustrates a schematic of mapping between concentration ranges of the input chemical species and output patterns of the output chemical species in the chemical circuit 110. Note that the number of output chemical species in the example depicted in FIG. 2 is five although the number of outputs can be arbitrarily increased. As described above, the pattern is presented as a result of progress of the chemical reaction network, more specifically, as steady state or end state of the chemical reaction network.

In FIG. 2, there are mappings between five concentration ranges and five output patterns. Note that symbols $O_i$ represent the output chemical species where i represents an index of the output chemical species. Notation $[O_i]$ denotes the concentration of the output chemical species with index i. Hence, the output pattern is represented by a vector of the concentrations of the plurality of output species ($[O_1]$, $[O_2]$, $[O_3]$, $[O_4]$, $[O_5]$). Also, note that the number of wavy lines depicted in relation to the input concentration ranges in FIG. 2 schematically expresses the concentration or the quantity of the molecules of the input chemical species. The wavy solid and dash lines depicted in relation to the output patterns schematically represent the presence and the absence of the molecules of the output chemical species $O_i$, respectively.

As the concentration of the input chemical species changes, the dominant (or major) species among the plurality of output chemical species $O_1$~$O_5$ switches. More specifically, as the concentration of the input chemical species increases, a lower-indexed output chemical species becomes dominant or major in turn as depicted in FIG. 2. Note that in FIG. 2 the concentrations of the output chemical species other than the dominant (or major) species are depicted to be zero, for convenience. However, the concentration of other species may be a small non-zero value.

The concentration of the dominant output chemical species in each output pattern may not be identical to each other ($[O_1] \neq [O_2] \neq [O_3] \neq [O_4] \neq [O_5]$) and the exact value of the concentration itself is less important. At least the presence or the absence of the output chemical species carries information. Thus, the output pattern can represent a digital signal having '1' (meaning dominant or major) at a digit corresponding to the dominant species. Such digital value can be easily detected and then used to compute a level of the concentration of the input chemical species by using the mapping shown in FIG. 2. Although the example shown in FIG. 2 is five level case, the readout resolution of the concentration can be improved by increasing the number of output chemical species involved in the chemical reaction network of the concentration classifier 110.

Figure 3:
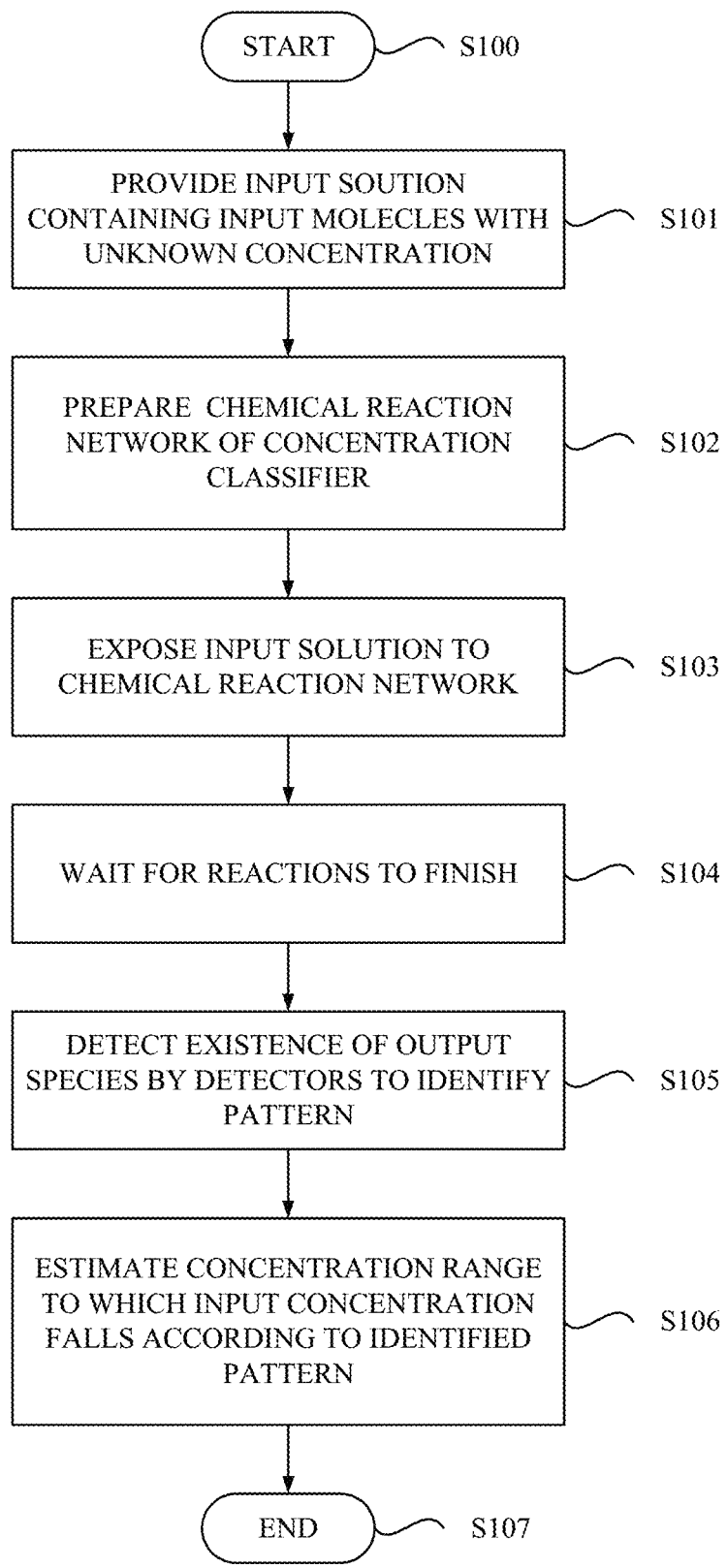
FIG. 3 illustrates a flowchart of a process for estimating a concentration range of a given input chemical species by way of the chemical circuit according to the exemplary embodiment of the present disclosure.

Referring to FIG. 3, a process for estimating a concentration of an input chemical species using chemical reactions is described. FIG. 3 illustrates a flowchart of the process for estimating the concentration of the input chemical species by way of the chemical circuit 110 according to the exemplary embodiment of the present disclosure.

The process shown in FIG. 3 may begin at step S100. The process may include a step of providing input solution containing the input chemical species having a certain concentration (S101). The process may also include a step of preparing the chemical reaction network of the concentration classifier 110 (S102). The chemical reaction network will be described in more detail latter.

Note that the order of the step of providing the solution (S101) and the step of preparing the chemical reaction network (S102) is arbitrary. Also, it will be understood by those skilled in the art that the terms 'provide', 'prepare', 'supply' and variants thereof, are used interchangeably herein to describe a provision of certain kind of chemical substance to an appropriate place, including a reactor, a reservoir or any other suitable place. Also, provision of the chemical reaction network means provision of a reactant, a catalyst, and/or an auxiliary substance that are involved in a set of chemical reactions constructing the chemical reaction network.

The process may further include a step of exposing the input solution to the prepared chemical reaction network so as to present an output pattern formed by the output chemical species in a manner depending on the concentration of the input chemical species (S103). As used herein, exposing the input solution to the prepared chemical reaction network means mixing the input solution and solution of the prepared chemical reaction network, contacting the input solution and solution of the prepared chemical reaction network, dropping the input solution into the solution of the prepared chemical reaction network or dropping the solution of the prepared chemical reaction network into the input solution, thereby causing the reaction to proceed.

The process may include a step of waiting for the chemical reaction network to finish or approach a steady state (S104). Note that the output pattern indicates a dominant species among the plurality of output chemical species as a result of progress of the chemical reaction network.

The process may further include a step of detecting at least presence of each output chemical species to identify the output pattern of the output chemical species (S105). The process may further include a step of estimating, by processing circuitry, a concentration range, to which the given concentration of the input chemical species falls, according to the output pattern of the output chemical species (S106), which is identified at the step S105. In the step S106, the processing circuitry may refer calibration parameters that represents relationship between predetermined patterns and predetermined ranges of concentration, which are related to the mapping shown in FIG. 2. The calibration parameters may be stored in appropriate memory device. The calibration parameters will be described in more detail latter. Then, the process may end at step S107.

Figure 4:
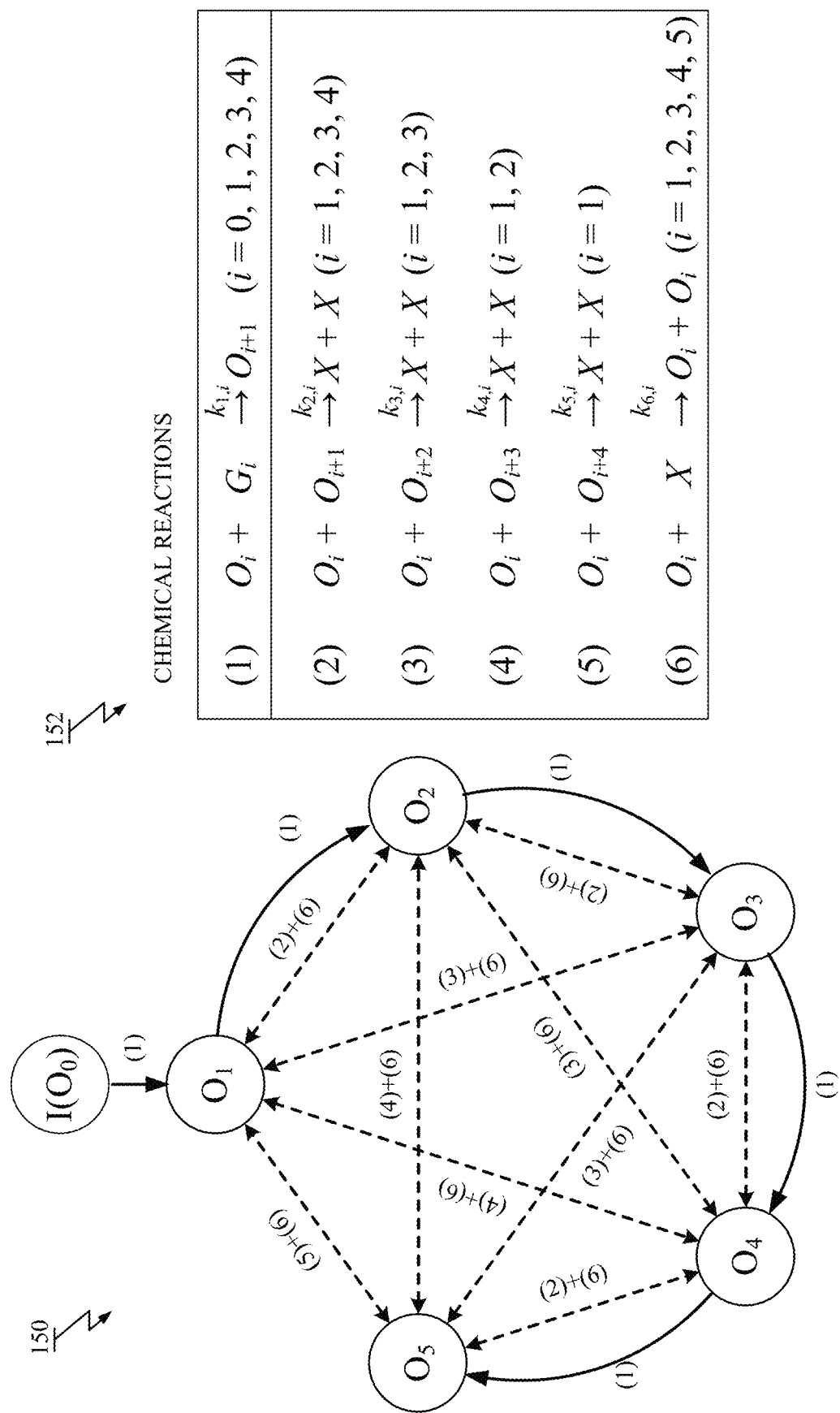
FIG. 4 illustrates a schematic of the chemical reaction network embodied in the chemical circuit according to the exemplary embodiment of the present disclosure.

With reference to FIG. 4, a chemical reaction network 150 embodied in the concentration classifier 110 according to the exemplary embodiment of the present disclosure is described in more detail. In FIG. 4, an architecture of the chemical reaction network 150 of the concentration classifier 110 and corresponding master equations 152 of the concentration classifier 110 are shown.

In the diagram of the architecture of FIG. 4, the input and output chemical species involved in the chemical reaction network 150 are represented by circles as nodes. The input chemical species is represented by I ($O_0$) and the output chemical species are represented by $O_i$ where i (0<i<=N) represents the index of the output chemical species. Note that the number of output chemical species, N, in the example depicted in FIG. 4 is five although the number of outputs can be arbitrarily increased. Each chemical reaction in the chemical reaction network 150 is represented by a straight or curved arrow as an edge connecting two nodes involved. The direction of the arrow denotes the direction of the chemical reaction.

As shown in FIG. 4, the chemical reaction network 150 includes at least a sequence of chemical reactions (1) (for i=0, 1, 2, 3, 4) starting with the input chemical species I ($O_0$) to generate a plurality of output chemical species $O_1$~$O_5$ in sequence. The sequence of chemical reactions (1) is a set of linked chemical reactions, where a product of a reaction becomes a reactant of a following reaction. Each chemical reaction (1) is denoted by a solid curved arrow in the diagram of the architecture shown in FIG. 4.

As described in the master equations 152 shown in FIG. 4, each chemical reaction (1) converts a lower one of the output chemical species $O_i$ into an upper one of the output chemical species $O_{i+1}$, in which the reactions start from the input chemical species I (or $O_0$) as the lowermost and end at the last output chemical species $O_5$ as the uppermost. Hence, the chemical reaction (1) is referred to as an up-conversion reaction herein. Each up-conversion reaction (1) involves a corresponding gate species $G_i$ (for i=0, 1, 2, 3, 4), which is consumed to convert the lower output species $O_i$ into the upper output species $O_{i+1}$. The set of gate species $G_0$~$G_4$ are preferably given at respective initial concentrations that decreases towards the upper side along the sequence of chemical reactions (1) ($[G_0]>[G_1]>[G_2]>[G_3]>[G_4]$).

As shown in FIG. 4, the chemical reaction network 150 includes further a set of chemical reactions (2)-(6) for forming consensus among the plurality of output chemical species $O_1$~$O_5$ that are generated from the up-conversion reactions (1) so as to single out major chemical species.

The set of chemical reactions (2)-(6) can be divided into two types of chemical reactions. Each of the first reactions (2)-(5) converts a pair of different output chemical species $O_i$ and $O_j$ (j=i+1, i+2, i+3, i+4 for i=1, j=i+1, i+2, i+3, for i=2, . . . ) into a buffer species X. Each of the second reactions (6) converts the buffer species X into one of the output chemical species $O_i$ using the output chemical species $O_i$ itself. Note that the buffer species X is shared by all the reactions for the consensus formation. The combination of the first reaction and the second reaction forms both of up-conversion reactions (a link of the first reaction: $O_i+O_{i+1} \rightarrow X+X$ and the second reaction: $O_{i+1}+X \rightarrow O_{i+1}+O_{i+1}$ forms an up-conversion reaction $O_i \rightarrow O_{i+1}$ as a whole) and down-conversion reactions (a link of the first reaction: $O_i+O_{i+1} \rightarrow X+X$ and the second reaction: $O_i+X \rightarrow O_i+O_i$ forms a down-conversion reaction $O_{i+1} \rightarrow O_i$ as a whole) via the intermediate buffer species X. Each combination of the first reaction and the second reaction ((2)+(6), (3)+(6), . . . (5)+(6)) is represented by a dashed straight bidirectional arrow in the diagram of the architecture in FIG. 4. The dashed arrow is bidirectional since there are the up-conversion reaction and the down-conversion reaction.

Hence, the chemical reaction network 150 shown in FIG. 4 is a composite of two types of networks; one is one-way sequential reactions, which is called 'up-converters', and other is consensus networks. Note that the consensus network shown in FIG. 4 is extended multi-species consensus network that involves all of the output chemical species more than two (five output species in this example) sharing the single buffer species X, in contrast to the related two-species consensus network.

In the master equations 152 of the concentration classifier 110 shown in FIG. 4, $k_{j,i}$ is a reaction rate constant, where j indicates the reaction equation numbers and i is the index of the output chemical species. Note that $k_{i,j}$ is defined only for i listed in the parenthesis following each equation.

The chemical reaction dynamics or the kinetics of the chemical reactions may be governed by a set of differential equations as follows:

$$\frac{d[G_i]}{dt} = -k_{1,i}[O_i][G_i], \tag{1}$$

-continued $(i = 0, 1, 2, 3, 4),$ $$\frac{d[O_i]}{dt} = k_{1,i-1}[O_{i-1}][G_{i-1}] - k_{1,i}[O_i][G_i] - k_{2,i}[O_i][O_{i+1}] - \qquad (2)$$
$$k_{3,i}[O_i][O_{i+2}] - k_{4,i}[O_i][O_{i+3}] - k_{5,i}[O_i][O_{i+4}] + k_{6,i}[O_i][X],$$

$(i = 0, 1, 2, 3, 4, 5)$ $$\frac{d[X]}{dt} = \sum_{i=1}^{4} 2k_{2,i}[O_i][O_{i+1}] + \sum_{i=1}^{3} 2k_{3,i}[O_i][O_{i+2}] + \qquad (3)$$
$$\sum_{i=1}^{2} 2k_{4,i}[O_i][O_{i+3}] + 2k_{5,1}[O_1][O_5] - \sum_{i=1}^{5} k_{6,i}[O_i][X].$$

In the aforementioned differential equations (1)-(3), the reaction rate constant k for undefined i can be regarded as zero. The reaction rate constant $k_{j,i}$ may have a value in an appropriate range.

When a DNA strand displacement (DSD) reaction (or, more generally, a nucleic acid strand displacement reaction that is the overall name for DNA and RNA strand displacement (DSD) reactions) is employed as the building block of the chemical reaction network 150, each reaction rate constant $k_{j,i}$ may have a value in a range of $1.0\sim1.0\times10^6$ $M^{-1}s^{-1}$ since the rate constant of the DSD reaction can be affected by the number of bases and GC (guanine-cytosine) contents of toeholds of the nucleic acid strand over 6 orders of magnitude under an assumption that there is no secondary structure in the toehold domain.

Note that in the master equations 152 shown in FIG. 4 a reverse reaction for each formal reaction is not incorporated. In general, some chemical reactions have reverse reactions. However, there is a way to suppress any reverse reaction in the DSD reaction framework. Therefore, ignoring the reverse reaction makes sense for certain chemical reactions, such as the DSD reaction. Biological implementation of the chemical reaction network 150 by way of the DSD reaction as well as the way to suppress the reverse reaction will be described latter.

In order to understand the mechanism of the concentration classifier 110 composed of the up-converters and the consensus network, the functions of the up-converters and the consensus network are considered separately. In the case that the consensus network does not takes place (the chemical reaction (2)-(6) shown in FIG. 4 are absent), the up-converters (merely the chemical reaction (1)) convert lower indexed chemical species $O_i$ into higher indexed output chemical species $O_{i+1}$ while consuming the gate species ($G_i$) until the input chemical species I ($O_0$) or the gate species $G_i$ are used up.

FIGS. 5A-5D show plots of the concentrations of the output chemical species $[O_i]$ versus the initial concentration of the input chemical species [I] provided by chemical reaction networks under several conditions. The plots shown in FIGS. 5A-5D are obtained by computational and numerical simulation based on the aforementioned set of differential equations (1)-(3). For simplicity, it is assumed that all the rate constants for the up-conversion reactions (1), $k_{1,i}$ for i=0, 1, 2, 3, 4, are the same and also the rate constants for the consensus network (2)-(6), $k_{2,i}$, $k_{3,i}$, $k_{4,i}$, $k_{5,i}$ and $k_{6,i}$, are the same. The rate constants of the up-conversion reactions ($k_{1,i}$) and the rate constants inside the consensus network ($k_{2,i}$, $k_{3,i}$, $k_{4,i}$, $k_{5,i}$, $k_{6,i}$) are represented by $k_{UC}$ and $k_{CN}$, respectively. First, it is assumed that all rate constants to be $1.0\times10^4$ $M^{-1}s^{-1}$ unless otherwise indicated. This value is in a realistic range of the rate constant for bimolecular DNA strand displacement (DSD) reaction.

Figure 5A:
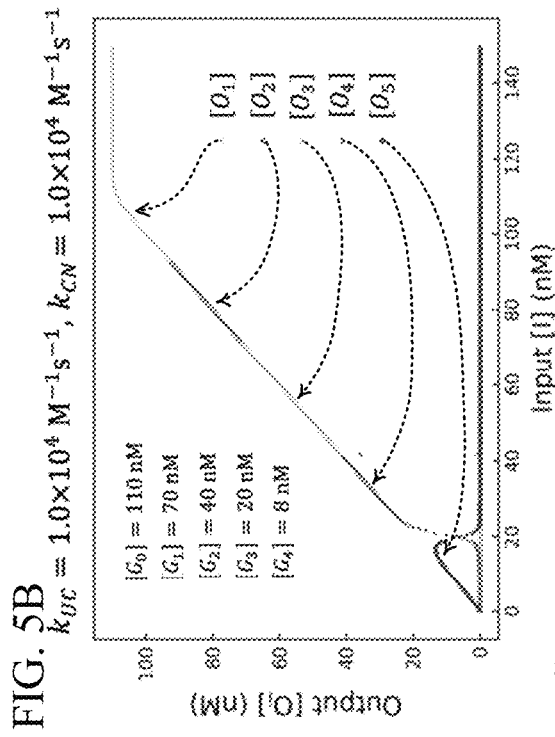
FIGS. 5A-5D show plots of concentrations of output chemical species versus an initial concentration of an input chemical species under several conditions in the chemical reaction network shown in FIG. 4 that are computationally simulated.

FIG. 5A shows a plot of the concentrations of the output chemical species versus the initial concentration of the input chemical species that is provided only by the up-converters (i.e., $k_{CN}$=0) after 20 hours reaction time. The concentrations of the gate species, $[G_i]$, are indicated on the plot. As shown in FIG. 5A, the major output chemical species changes successively according to the initial concentration of the input chemical species, [I]. This behavior is derived from the gradation of the initial concentrations of the gate species $([G_0]>[G_1]>[G_2]>[G_3]>[G_4])$.

As the initial concentration of the input chemical species, [I], increase from zero, the gate species $G_4$ is used up at a certain input level so that the subsequent increase of the input chemical species causes the accumulation of the output species $O_4$. As the initial concentration, [I], further increase, the gate species $G_3$ is used up at a certain input level so that the output species $O_3$ is accumulated. In this manner, the major species switches in turn. This switching behavior plays a role to single out the dominant (or major) species in the consensus network.

Figure 5B:
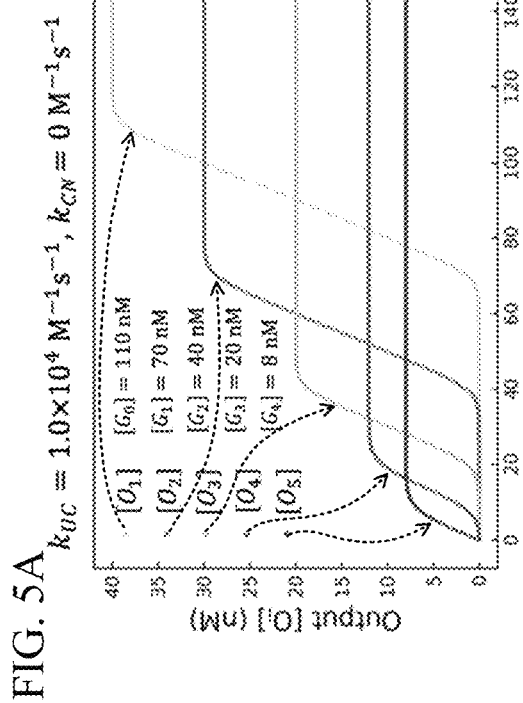

FIG. 5B shows a plot of the concentrations of the output chemical species versus the initial concentration of the input chemical species that is provided by the combination of both the up-converters and the consensus network after 20 hours reaction time. Along with the successive production of the output chemical species driven by the up-converters (chemical reaction (1)), the consensus network (chemical reaction (2)-(6)) leaves the major species while attenuating other minor species. The consensus network in the concentration classifier 110 shown in FIG. 4 is composed of ten non-catalytic reactions (chemical reaction (2)-(5)) and five catalytic reactions (chemical reaction (6)). In the consensus network reactions, all the output species $O_i$ react each other first to generate the buffer species X by the non-catalytic reactions (2)-(5). Subsequently, the buffer species X are consumed by the catalytic reactions (6). The reaction rate of the catalytic reactions may be in proportion to the concentration of each output chemical species, and as a result the population of the major output species grows faster and finally dominates. The remaining species composition after 20 hours is shown in FIG. 5B. In a wide range of the initial concentration of the input chemical species, [I], only single output species becomes dominant. The concentration of the output chemical species $[O_i]$ increases proportionately as the input concentration, [I], increases, and subsequently the output chemical species switches at certain input concentrations where each gate species is used up. Finally, the concentration of the output chemical species saturates when the gate strand $G_0$ is used up.

The switching behavior may be governed by the concentrations of the gate species and the reaction rate constants. As already mentioned, the initial concentrations of the gate species have a gradation so as to switch the major species according to the input concentration [I]. The switching values that indicates the input concentrations on which the output species switch from one species to another species are mainly determined by the concentration of each gate species.

Figure 5C:
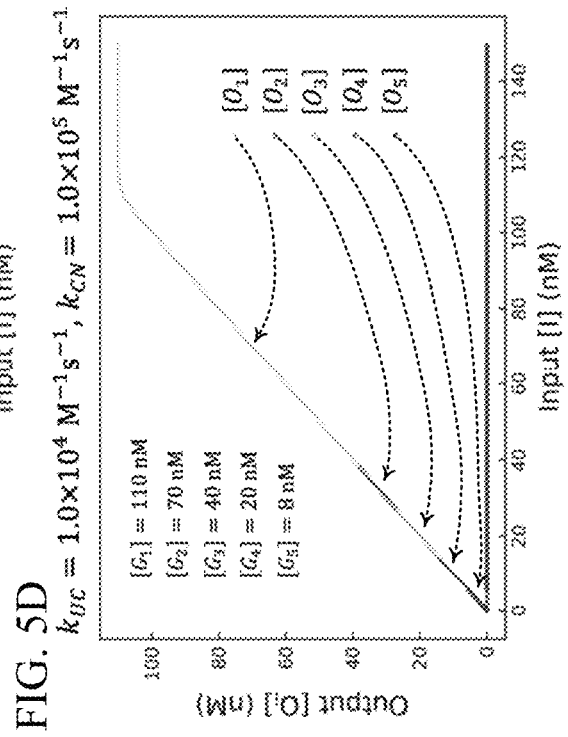
Figure 5D:
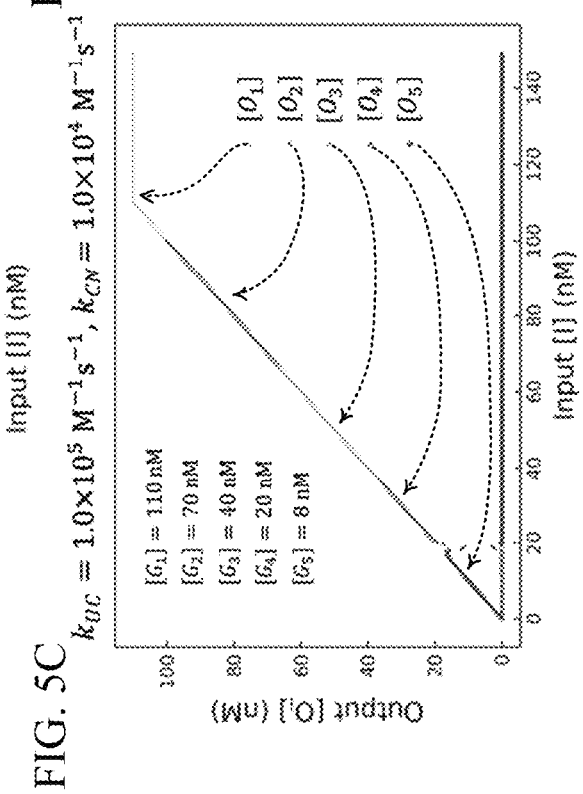

FIG. 5C and FIG. 5D shows plots of the concentrations of the output chemical species versus the initial concentration of the input chemical species that are provided by both the up-converters and the consensus network, in which the rate constants are different from that of FIG. 5B.

FIG. 5C shows a plot of a case where relatively higher rate constants of the up-converters than those of the consensus network ($k_{UC}$>$k_{CN}$) are used. Regarding the rate constants, the relative ratio of rate constants is focused since absolute values only change the timescale. As shown in FIG. 5C, relatively higher rate constants of the up-converters ($k_{UC}$) than those of the consensus network ($k_{CN}$) result in more drastic switching behavior, because the concentrations of the output species more directly follow the concentrations generated by the up-converters.

FIG. 5D shows a plot of a case where relatively lower rate constants of the up-converters than those of the consensus network ($k_{UC}$<$k_{CN}$) are used. With a higher-rate consensus network, more species are converted into higher-indexed output species than the case of the lower-rate consensus network shown in FIG. 5C. This is because an amount of the higher-indexed species always exceeds than that of the lower-indexed species due to the gradation of the concentrations of the gate species. As a result, the switching values shift to the lower side of the input concentration in comparison with the relatively lower rate constants of the consensus network, $k_{CN}$. Therefore, the dynamic range of the concentration classifier 110 can be tuned by both the concentrations of the gate species and the rate constants of each reaction. Note that isolation of a region where a single output strand is dominate is not so clear in the lower input region while it is clear in the higher input region. This is because the reaction rate becomes slower as the input concentration becomes lower since the lower concentration of the reactants results in longer time required to reach a steady state.

As shown in FIGS. 5B-5D, the switching values, which correspond to the boundaries between the concentration ranges in the mapping shown in FIG. 2, may depend on parameters of the chemical reaction network involved in the concentration classifier 110. Note that the switching values indicates the input concentrations on which the output chemical species switches from one chemical species to another chemical species. Such parameters include the rate constants of the chemical reactions and the concentration of the reactants. Hence, the calibration can be preferably performed. By measuring samples of the input chemical species with known concentrations, a set of calibration parameters that represents relationship between predetermined patterns and predetermined ranges of concentration can be obtained. Using of the calibration parameters enables us to improve the estimation accuracy.

Figure 6:
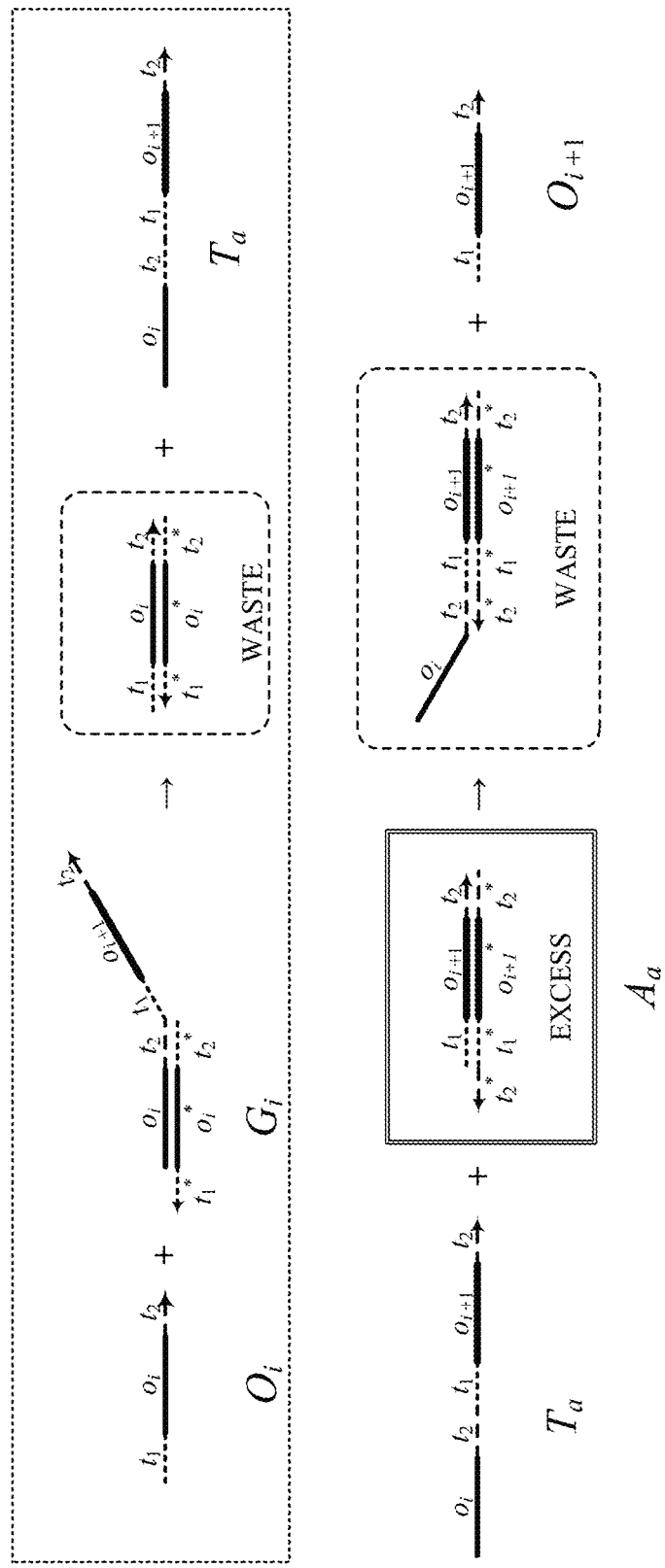
FIG. 6 shows biochemical implementation of up-conversion reactions (1) shown in FIG. 4 according to a particular embodiment of the present disclosure.
Figure 7:
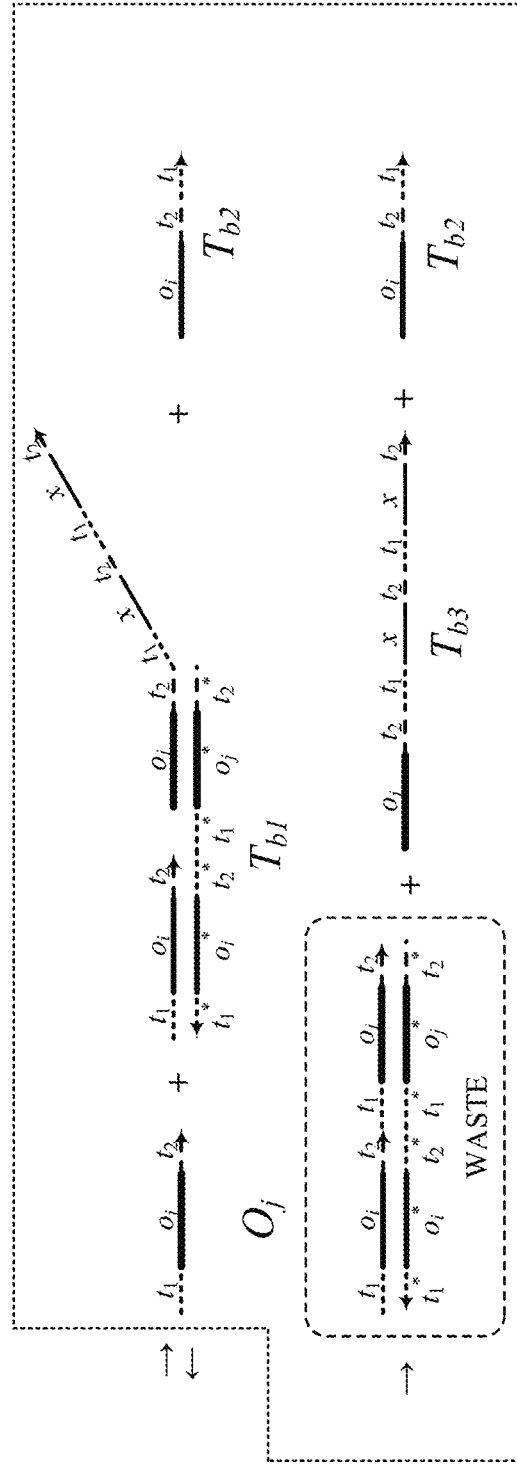
FIG. 7 shows biochemical implementation of non-catalytic reactions (2)-(5) for consensus formation shown in FIG. 4 according to the particular embodiment of the present disclosure.
Figure 8:
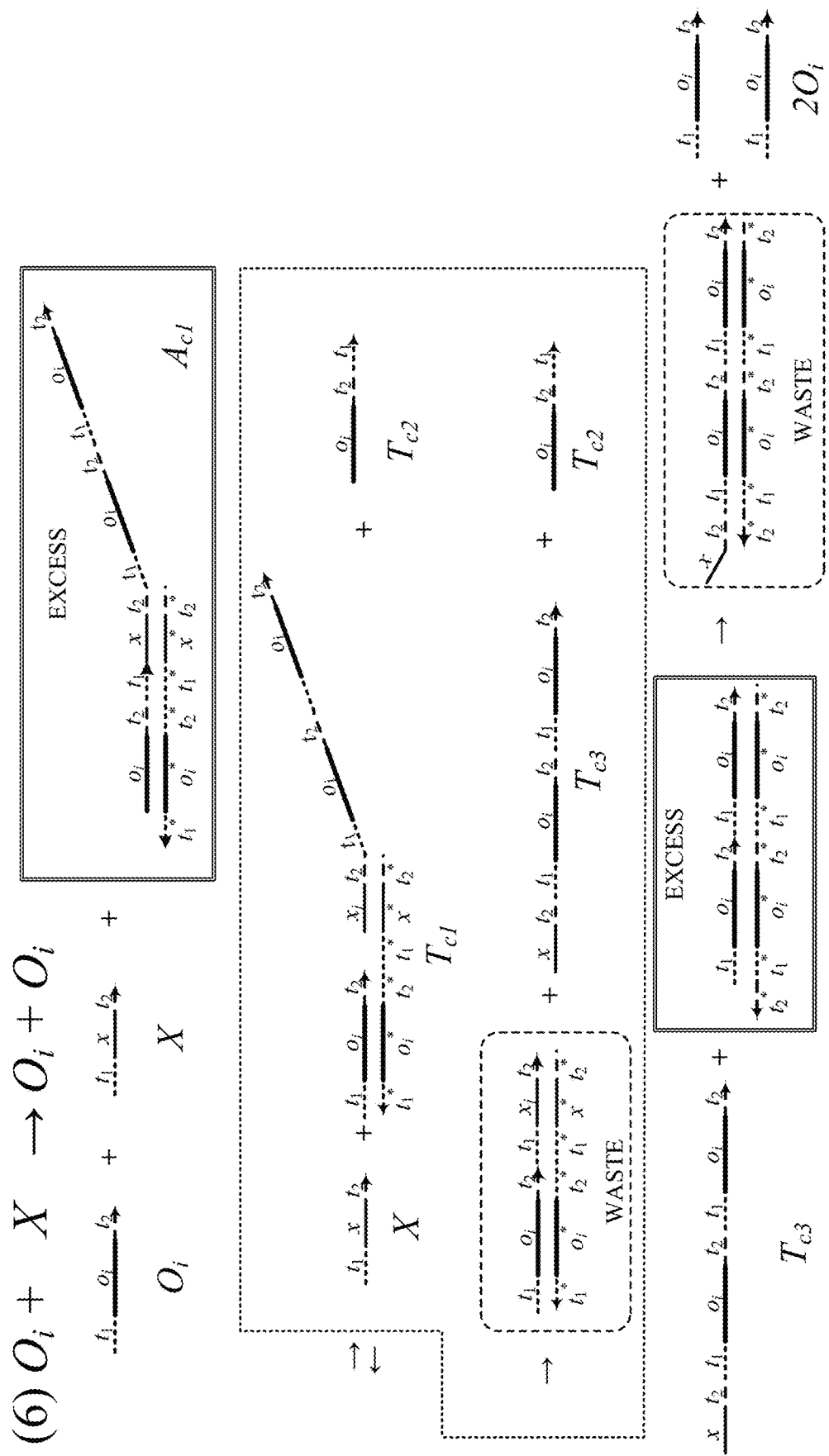
FIG. 8 shows biochemical implementation of catalytic reactions (6) for consensus formation shown in FIG. 4 according to the particular embodiment of the present disclosure.

Biochemical implementation of the chemical reaction network 150 shown in FIG. 4 is described with reference to FIGS. 6-8. FIG. 6 shows the biochemical implementation of the up-conversion chemical reactions (1). FIG. 7 shows the biochemical implementation of the non-catalytic chemical reactions (2)-(5) for the consensus formation. FIG. 8 shows the biochemical implementation of the catalytic chemical reactions (6) for the consensus formation.

According to the biochemical implementation shown in FIGS. 6-8, a chemical circuit device, as described herein, may act as an artificial biological synthetic circuit. In such an implementation, the input chemical species and the output chemical species are nucleic acid strands (e.g., DNA or RNA single strands). In the biochemical implementation shown in FIGS. 6-8, DNA strand displacement (DSD), more generally, nucleic acid strand displacement reactions, which is a versatile and universal reaction that can implement arbitrary chemical reaction networks with many types of both digital and analog functions, is utilized to embody the aforementioned chemical reactions (1)-(6). Note that the biological implementation shown in FIGS. 6-8 is merely an example and different implementations may also be contemplated.

The nucleic acids are biopolymers. The term 'nucleic acid' is a general term for DNA and RNA. The nucleic acid is composed of nucleotides, which are the monomers made of three components, including a 5-carbon sugar, a phosphate group and a base. If the sugar is a ribose, the nucleic acid is RNA. If the sugar is derived from ribose as deoxyribose, the nucleic acid is DNA. Note that terms the 'nucleic acid', 'DNA' and 'RNA' are referred to chemical compounds rather than a specific nucleic acid, DNA and RNA relating to the living cells.

The nucleic acid strand displacement reactions are reactions to exchange one output strand of DNA or RNA with another input strand. The nucleic acid strand displacement reaction is based on the hybridization of two complementary strands of DNA or RNA via Watson-Crick base pairing, in which adenine (A) forms a base pair with thymine (T) for DNA or uracil (U) for RNA using two hydrogen bonds, and guanine (G) forms a base pair with cytosine (C) using three hydrogen bonds. The nucleic acid strand displacement reaction utilizes the thermodynamics of the nucleic acids that proceed into states having bigger number of hybridized base pairs, which is more thermodynamically stable. The nucleic acid strand displacement reaction is enzyme-free and hence input DNA/RNA molecules drive reactions only by being mixed with reagents that include DNA/RNA molecules.

Each of the input and output strands has a representative domain and a toehold domain. The representative domain is unique to the chemical species and determines signal identity. The input strand and respective output strands have respective representative domains each having a unique base sequence. The toehold domain acts as a scaffold for initiating binding to other nucleic acid strand in the nucleic acid strand displacement reaction.

In FIGS. 6-8, DNA (or RNA) strands are represented by arrows, which direct from 5'-end to 3'-end. The representative domain of each strand species is represented by $o_i$, or $o_{i+1}$ and the toehold domains are represented by $t_1$, $t_2$. The single line with the arrow pointing to one side represents a single DNA/RNA strand. A pair of lines with two arrows pointing in opposite directions represents a hybridized strand. An asterisk (*) attached to a domain indicates that the domain is Watson-Crick complement of the counterpart domain denoted by the same letter. In addition to the strand species indicated in the reaction formula in FIG. 4 such as $O_i$, $G_i$, there are other strand species involved in the reactions, called auxiliary strands. The auxiliary strands are highlighted by the double line border boxes in FIGS. 6-8. It is assumed that there is an excessive amount of the auxiliary strands. Thereby, all formal reactions shown in FIG. 4 can be approximated to be bimolecular reactions because only bimolecular elementary reactions indicated by the dotted square boxes in FIGS. 6-8 are rate-limiting steps with non-excess amounts of reactants. In FIGS. 6-8, the dashed border round boxes indicate waste strands, which do not participate in any subsequent reactions including the reverse reaction of each elementary reaction. Although the reverse reactions would occur slightly, the reaction rates of the reverse reactions are so slow to be negligible.

As shown in FIG. 6, each up-conversion reaction (1) in the chemical reaction network 150 includes a cascade of nucleic acid strand displacement reactions. In a first reaction, the output strand $O_i$ reacts with the gate strand $G_i$ to output an intermediate strand $T_a$. The gate strand $G_i$ is a hybridized strand containing the intermediate strand $T_a$ and the complementary of the output stand $O_i^*$ that exposes the toehold $t_1^*$. Note that even though the DSD reaction can be reversible, the reaction rates of the reverse reactions are so slow to be negligible since the waste generated by the reaction is hybridized in a whole and there is no toehold left in the strands. In the second reaction, the generated intermediate strand $T_a$ reacts with the auxiliary strand $A_a$ with the excessive amount to output the upper-indexed output strand $O_{i+1}$ with sufficiently fast rate. The auxiliary strand $A_a$ is a hybridized strand containing the upper-indexed output strand $O_{i+1}$ and a strand having its complementary $O_{i+1}^*$ and the toehold $t_2^*$. Note that even though the waste has a part of single-stranded segments denoted by $o_i$, the waste would not participate in the reverse reaction since there is no strand having a complementary of the single stranded segment, $o_i^*$, as a toehold.

As shown in FIG. 7, each non-catalytic-reaction (2)-(5) in the chemical reaction network 150 includes also a cascade of nucleic acid strand displacement reactions. In a first reaction, an output strand $O_i$ reacts with a first auxiliary strand $A_{b1}$ to form an intermediate hybridized strand $T_{b1}$ that exposes a toehold $t_1^*$ for the subsequent reaction and to release a strand $T_{b2}$. In a second reaction, other output strand $O_j$ reacts with the intermediate hybridized strand $T_{b1}$ by way of the exposed toehold $t_1^*$ as a starting point to output the intermediate strand $T_{b3}$. The first auxiliary strand $A_{b1}$ is a hybridized strand containing a sequence of the intermediate strand $T_{b3}$ and the strand $T_{b2}$ and a strand having the complementary of the output stands $O_j^*$ and $O_i^*$ that exposes the toehold $t_1^*$. In the first and second reaction, the first auxiliary strand $A_{b1}$ reacts with the two output strands $O_i$ and $O_j$ to output the intermediate species $T_{b3}$. In the third reaction, the intermediate strand $T_{b3}$ reacts with a second auxiliary strand $A_{b2}$ to output two buffer strands 2X. The second auxiliary strand $A_{b2}$ is a hybridized strand containing a sequence of two buffer strand 2X and a strand having their complementary 2X*  and a toehold $t_2^*$. Note that even though the first reaction is a reversible reaction, the second reaction performs unidirectionally since the waste generated by the second reaction is hybridized in a whole and there is no toehold remaining in the strands. Also, since the third reaction involves the second auxiliary strand $A_{b2}$ with the excessive amount, the third reaction proceeds with sufficiently fast rate so that the bimolecular elementary reaction indicated by the dotted square box in FIG. 7 is a rate-limiting step.

As shown in FIG. 8, each catalytic-reaction (6) in the chemical reaction network 150 includes also a cascade of nucleic acid strand displacement reactions. The cascade of nucleic acid strand displacement reactions shown in FIG. 8 is similar to that shown in FIG. 7. In a first reaction, an output strand $O_i$ reacts with a first auxiliary strand $A_{c1}$ to form an intermediate hybridized strand $T_{c1}$ that exposes a toehold $t_1^*$ for the subsequent reaction and to release a strand $T_{c2}$. In a second reaction, the buffer strand X reacts with the intermediate hybridized strand $T_{c1}$ to output an intermediate strand $T_{c3}$. In the third reaction, the intermediate strand $T_{c3}$ reacts with a second auxiliary strand $A_{c2}$ to output two output strands $2O_i$. As similar to the reactions shown in FIG. 7, the bimolecular elementary reaction indicated by the dotted square box in FIG. 8 is a rate-limiting step.

As mentioned above, it is known that a rate constant of the DSD reaction can be controlled by the number of bases and GC contents of the toeholds over 6 orders of magnitude under an assumption that there is no secondary structure in the toehold domain. Therefore, $10^4$ and $10^5 M^{-1} s^{-1}$ used in the aforementioned computational analysis is a plausible value for the rate constant of the DSD reaction. The rate constant for the cascade of nucleic acid strand displacement reactions is affected by the number of bases and GC content of toehold domains of a nucleic acid strand involved therein.

The aforementioned DNA/RNA strands with specific base sequence shown in FIGS. 6-8 can be synthesized biochemically by using plasmids for example, or synthesized chemically. Since any nucleic acid with a desired sequence can be synthesized by ways of any known appropriate technique, details of the DNA/RNA synthesis method are omitted.

Figure 9:
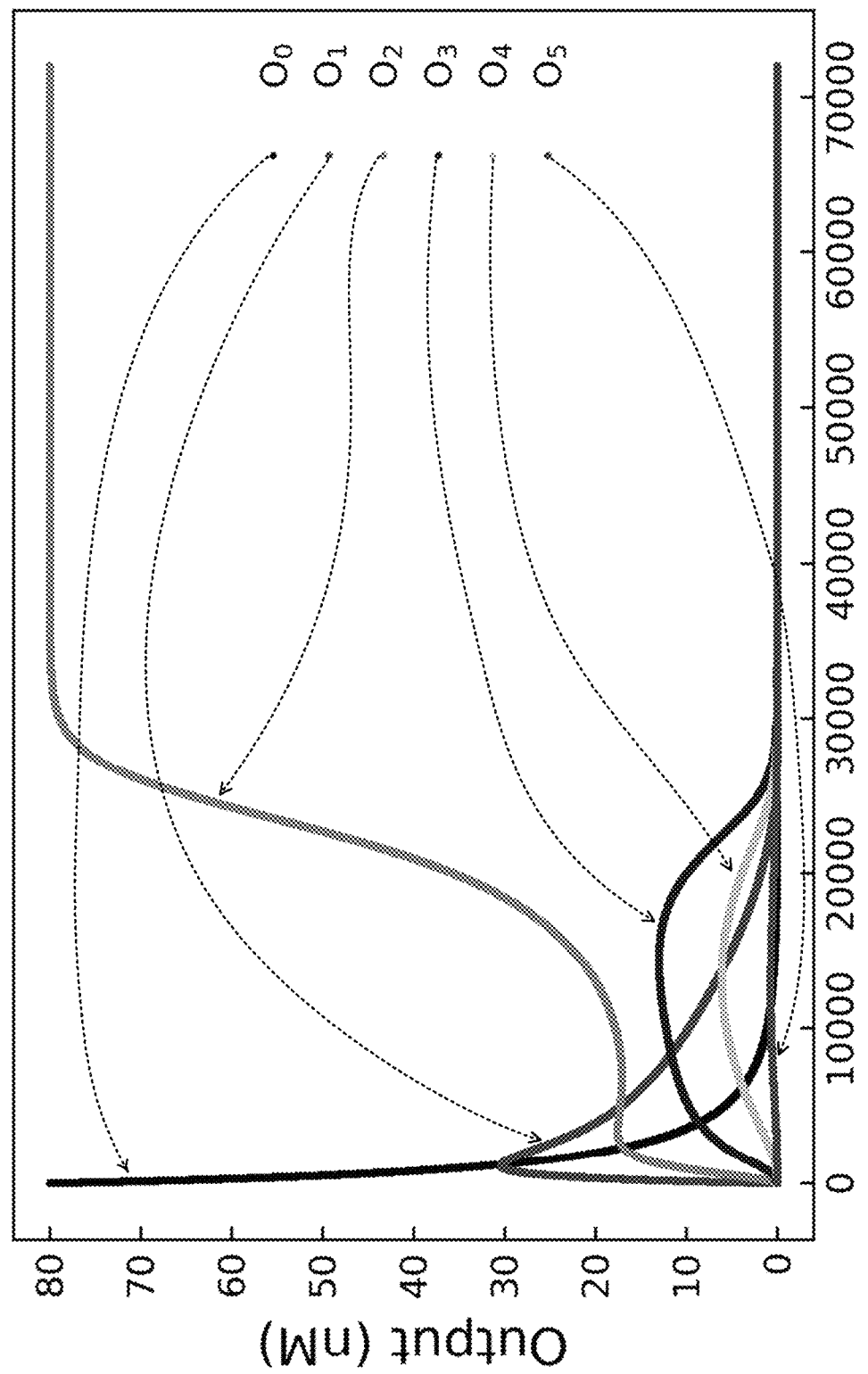
FIG. 9 shows transient behavior observed in a composition of the output chemical species under a condition that are computationally simulated.

FIG. 9 shows transient behavior observed in the composition of the output chemical species under a condition. The timeseries shown in FIG. 9 is obtained by computational and numerical simulation based on the aforementioned set of differential equations (1)-(3). The transient behavior shown in FIG. 9 is obtained under the condition where the initial concentration of the input chemical species is a specific value, [I]=80 nM.

As shown in FIG. 9, the chemical reaction network finally approaches a steady state where the 2nd output chemical species $O_2$ becomes dominant and remaining output chemical species $O_1$, $O_3 \sim O_5$ become approximately zero. During the transient phase, the output chemical species $O_1$, $O_3 \sim O_5$ other than the final dominant species $O_2$ may show an increase, but which is temporary. Thus, the concentration of the input chemical species can be estimated by detecting the presence of each output chemical species after a sufficient time has elapsed. Although the concentration of the input chemical species is preferable to be detected after the sufficient time has elapsed, there is a possibility that the measurement can be finished at an earlier stage than the system reaches the steady state where no change in composition occurs in view of the transient behavior shown in FIG. 9. For example, the measurement of the presence or the level of the concentration of the output chemical species at multiple points of time even during the transient phase would suggest a species that finally becomes dominant.

The chemical circuit 110 and the process based on the chemical reaction network 150 shown in FIG. 4, in which the chemical reaction network 150 is composed of the up-converters and the consensus network, has been described. Hereinbelow, referring to FIG. 6 and FIGS. 10-12, a chemical circuit and process based on a chemical reaction network different from one shown in FIG. 4 is described.

Figure 10:
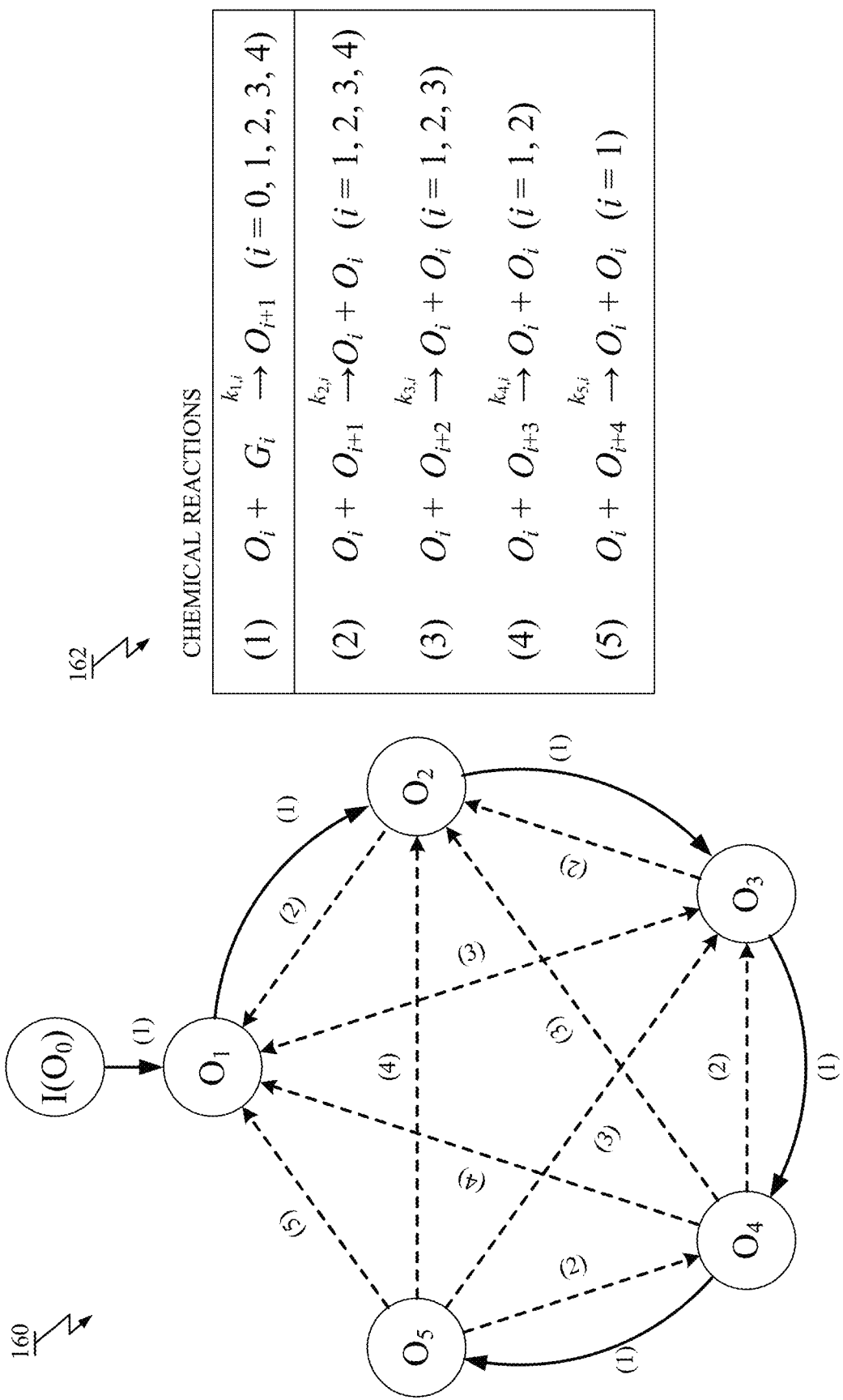
FIG. 10 illustrates a schematic of a chemical reaction network embodied in a chemical circuit according to other exemplary embodiment of the present disclosure.

With reference to FIG. 10, a chemical reaction network 160 embodied in a concentration classifier 110 according to other exemplary embodiment of the present disclosure is described. In FIG. 10, an architecture of the chemical reaction network 160 and corresponding master equations 162 of the concentration classifier 110 according to other exemplary embodiment of the present disclosure are shown. Similar to FIG. 4, the input chemical species is represented by I ($O_0$) and the output chemical species are represented by $O_i$, where i (i>0) represents the index of the output chemical species. Note that the number of output chemical species in the example depicted in FIG. 4 is also five although the number of outputs can be arbitrarily increased.

As shown in FIG. 10, the chemical reaction network 160 includes also at least a sequence of chemical reactions (1) (for i=0, 1, 2, 3, 4) starting with the input chemical species I (or $O_0$) to generate a plurality of output chemical species $O_1 \sim O_5$ in sequence. The sequence of chemical reactions (1) is a set of linked up-conversion reactions, where a product of a reaction becomes a reactant of a following reaction. Each chemical reaction (1) converts a lower one of the output chemical species $O_i$ into an upper one of the output chemical species $O_{i+1}$, as similar to the chemical reaction network 150 shown in FIG. 4. Each chemical reaction (1) involves a corresponding gate species $G_i$ (for i=0, 1, 2, 3, 4), which is consumed to convert the lower output species $O_i$ into the upper output species $O_{i+1}$. The set of gate species $G_0 \sim G_4$ are given at respective initial concentrations that decreases towards the upper side along the sequence of chemical reaction (1), i.e., there is a gradation ($[G_0]>[G_1]>[G_2]>[G_3]>[G_4]$).

As shown in FIG. 10, the chemical reaction network 160 includes further a set of chemical reactions (2)-(5), each of which converts an upper output chemical species $O_{i+1}$ into a lower output chemical species $O_i$, with product sides along the sequence of chemical reactions (1) as upper sides. The upper output chemical species $O_{i+1}$ is down-converted into the lower output chemical species $O_i$ using the lower output chemical species $O_i$ itself.

Hence, the chemical reaction network 160 shown in FIG. 10 is a composite of two types of networks; one is up-converters, and other is down-converters. The down-converters still have similar functionality to the consensus network. However, there are two major differences between the consensus network and the down-converters. First, the down-converters do not involve any buffer species X, which is involved in the consensus network shown in FIG. 4, so output chemical species directly react each other. Second, the down-converters compete with the up-converters, whereas the consensus network involves competitions among the members of the consensus network for winning the majority. Therefore, in the chemical reaction network 160, the ratio of reaction rates of up-converters and down-converters play a role for determining the switching behavior.

In the master equations 162, $k_{j,i}$ is a reaction rate constant, where j indicates the reaction equation numbers and i is the index of the output chemical species.

The chemical reaction dynamics or the kinetics of the chemical reactions shown in FIG. 10 may be governed by a set of differential equations as follows:

$$\frac{d[G_i]}{dt} = -k_{1,i}[O_i][G_i], \quad (4)$$

$$(i = 0, 1, 2, 3, 4)$$

$$\frac{d[O_i]}{dt} = k_{1,i-1}[O_{i-1}][G_{i-1}] + k_{2,i-1}[O_{i-1}][O_i] + \quad (5)$$

$$k_{3,i-2}[O_{i-2}][O_i] + k_{4,i-3}[O_{i-3}][O_i] + k_{5,i-4}[O_{i-4}][O_i] - k_{1,i}[O_i][G_i] -$$

$$k_{2,i}[O_i][O_{i+1}] - k_{3,i}[O_i][O_{i+2}] - k_{4,i}[O_i][O_{i+3}] - k_{5,i}[O_i][O_{i+4}].$$

$$(i = 0, 1, 2, 3, 4, 5)$$

In the aforementioned differential equations (4)-(5), the reaction rate constant k for undefined i is regarded as zero. The reaction rate constant $k_{j,i}$ may have a value in an appropriate range. When the nucleic acid strand displacement reactions are employed as the building block of the chemical reaction network 160, the reaction rate constant $k_{j,i}$ may have a value in a range of $1.0 \sim 1.0 \times 10^6$ $M^{-1}s^{-1}$, as similar to the embodiment shown in FIG. 4 The reverse reaction for each formal reaction is not incorporated.

Figure 11B:
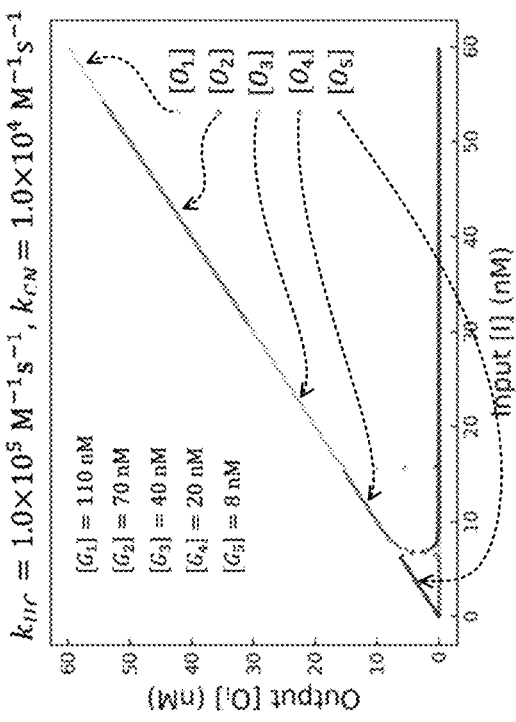
FIGS. 11A-11C show plots of concentrations of output chemical species versus an initial concentration of an input chemical species under several conditions in the chemical reaction network shown in FIG. 10 that are computationally simulated.
Figure 11A:
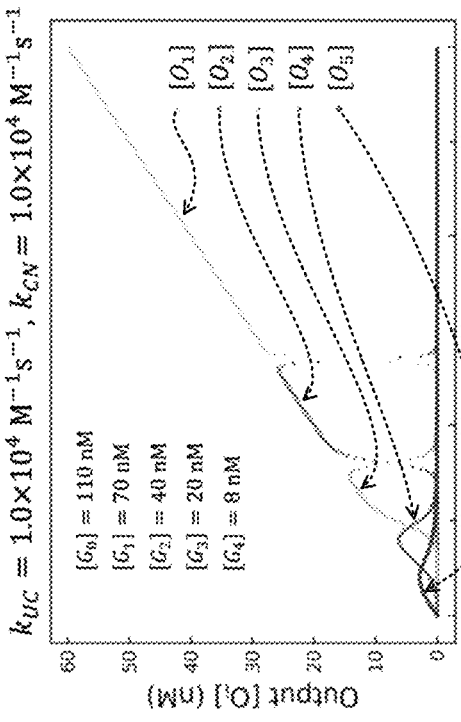
Figure 11C:
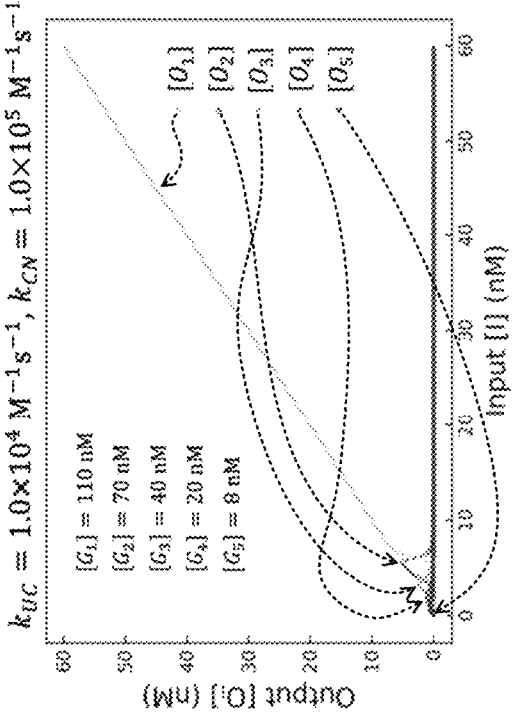

FIGS. 11A-11C show plots of the concentrations of the output chemical species $[O_i]$ versus the initial concentration of the input chemical species [I] that are provided by chemical reaction networks under several conditions. The plots shown in FIGS. 11A-11C are obtained by computational and numerical simulation based on the aforementioned set of differential equations (4)-(5). For simplicity, it is assumed that all $k_{1,i}$ are the same and also $k_{2,i}$, $k_{3,i}$, $k_{4,i}$ and $k_{5,i}$ are the same. The rate constants of the up-converters ($k_{1,i}$) and the rate constants of the down-converters ($k_{2,i}$, $k_{3,i}$, $k_{4,i}$, $k_{5,i}$) are represented by $k_{UC}$ and $k_{DC}$, respectively. It is also assumed that all rate constants to be $1.0 \times 10^4$ $M^{-1}s^{-1}$ unless otherwise indicated.

FIG. 11A shows a plot of the concentrations of the output chemical species versus the initial concentration of the input chemical species that is provided by the up-converters and the down-converters after 20 hours reaction time with $k_{UC}=1.0 \times 10^4$ $M^{-1}s$' and $k_{DC}=1.0 \times 10^4$ $M^{-1}s^{-1}$. In comparison with FIGS. 5B, even with the same gate species composition, the switching values are different from that of the chemical reaction network 150 shown in FIG. 4. The switching values of the chemical reaction network 150 shown in FIG. 4 are determined mainly by the gate species composition and partly affected by the rate constants. However, the switching values of the chemical reaction network 160 shown in FIG. 10 are strongly affected by the rate constants. FIG. 11B and FIG. 11C shows plots of the remaining strand compositions with different rate constants. With higher $k_{UC}$, the switching values shift to larger input concentrations. With higher $k_{DC}$ the switching values shift to lower input concentrations. This behavior can be simply interpreted as a result from the competition between the up-converters and the down-converters.

Figure 12:
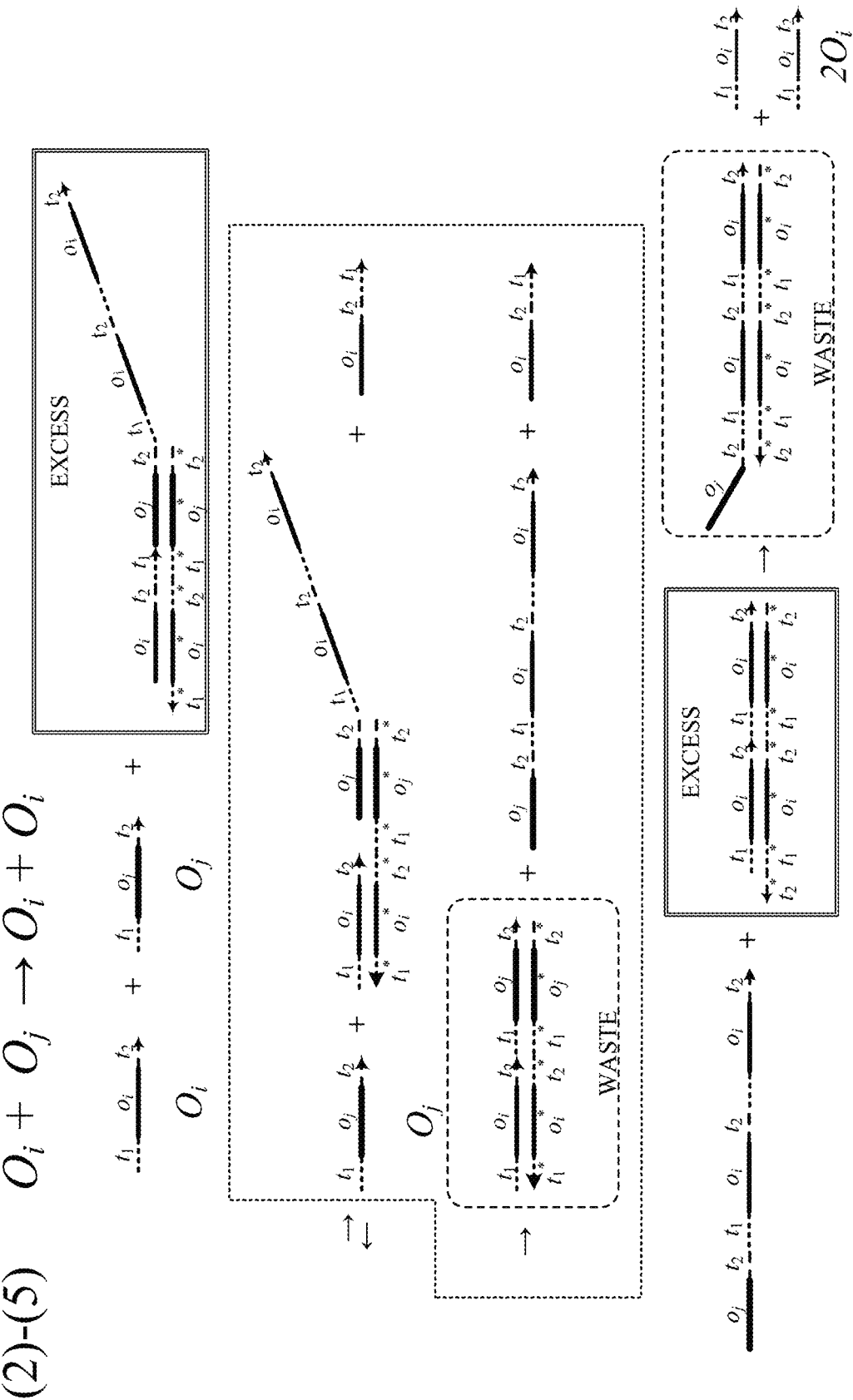
FIG. 12 shows biochemical implementation of down-conversion reaction (2)-(5) shown in FIG. 10 according to other particular embodiment of the present disclosure.

Biochemical implementation of the chemical reaction network 160 shown in FIG. 10 is described with reference to FIG. 6 and FIG. 11. The biochemical implementation of the up-conversion chemical reactions (1) in the chemical reaction network 160 is the same as that shown in FIG. 6. FIG. 12 shows the biochemical implementation of the chemical reactions (2)-(5) for the down-converters.

The chemical reaction network 150 shown in FIG. 4 and the chemical reaction network 160 shown in FIG. 10 are different in terms of switching behavior and biochemical cost. First, the switching behavior of the chemical reaction network 160 shown in FIG. 10 is more sensitive to the rate constants than that of the chemical reaction network 150 shown in FIG. 4. This sensitivity is a result of the competition between the up-converters and the down-converters in the chemical reaction network 160. This feature of the chemical reaction network 160 shown in FIG. 10 provides a tunability of dynamic range of the estimation whereas the chemical reaction network 150 shown in FIG. 4 has a stability of the behavior of the chemical circuit. Therefore, both chemical reaction networks 150,160 can be employed properly according to requirements from application stand points. Also, note that the switching behavior is also controlled by the concentration of the gate species.

With respect to the biochemical implementation cost of the chemical reaction networks 150, 160, the term "biochemical implementation cost" simply means the number of strand species involved in the chemical reaction networks 150, 160 when the biological implementation shown in FIGS. 6-8, 12 is employed. TABLE 1 shows a comparison of the number of strand species required to implement each chemical circuit when the number of the output strand species is N.

TABLE 1

| Types of strand species | The network shown in FIG. 4 | The network shown in FIG. 10 |
| --- | --- | --- |
| Output species | N | N |
| Buffer species | 1 | 0 |
| Gate species | N | N |
| Auxiliary species | $N^2 + 2N$ | $N^2$ |

The total biochemical cost is predominantly determined by the concentrations of the auxiliary strand species, because the auxiliary strand species is required to be larger than other species to keep the reaction system the set of bimolecular reactions as described by the master equations in FIG. 4. and FIG. 10. Note that although the absolute number of the auxiliary strand species depends on the specific biochemical implementation, the number of strand species in both networks 150, 160 can be compared to some extent. The chemical reaction network 160 shown in FIG. 10 requires a smaller number of auxiliary strand species to be biochemically implemented, because it does not involve buffer species X, which is required by the chemical reaction network 150 shown in FIG. 4. However, when N becomes larger, the term of $N^2$ becomes more dominant. Thus, both chemical reaction networks 150, 160 are comparable in terms of the cost for biochemical implementation.

Hereinbelow, referring to FIG. 13, a chemical circuit device implementing the chemical reaction network 150 shown in FIG. 4 or the chemical reaction network 160 shown in FIG. 10 according to an exemplary embodiment of the present disclosure is described.

Figure 13:
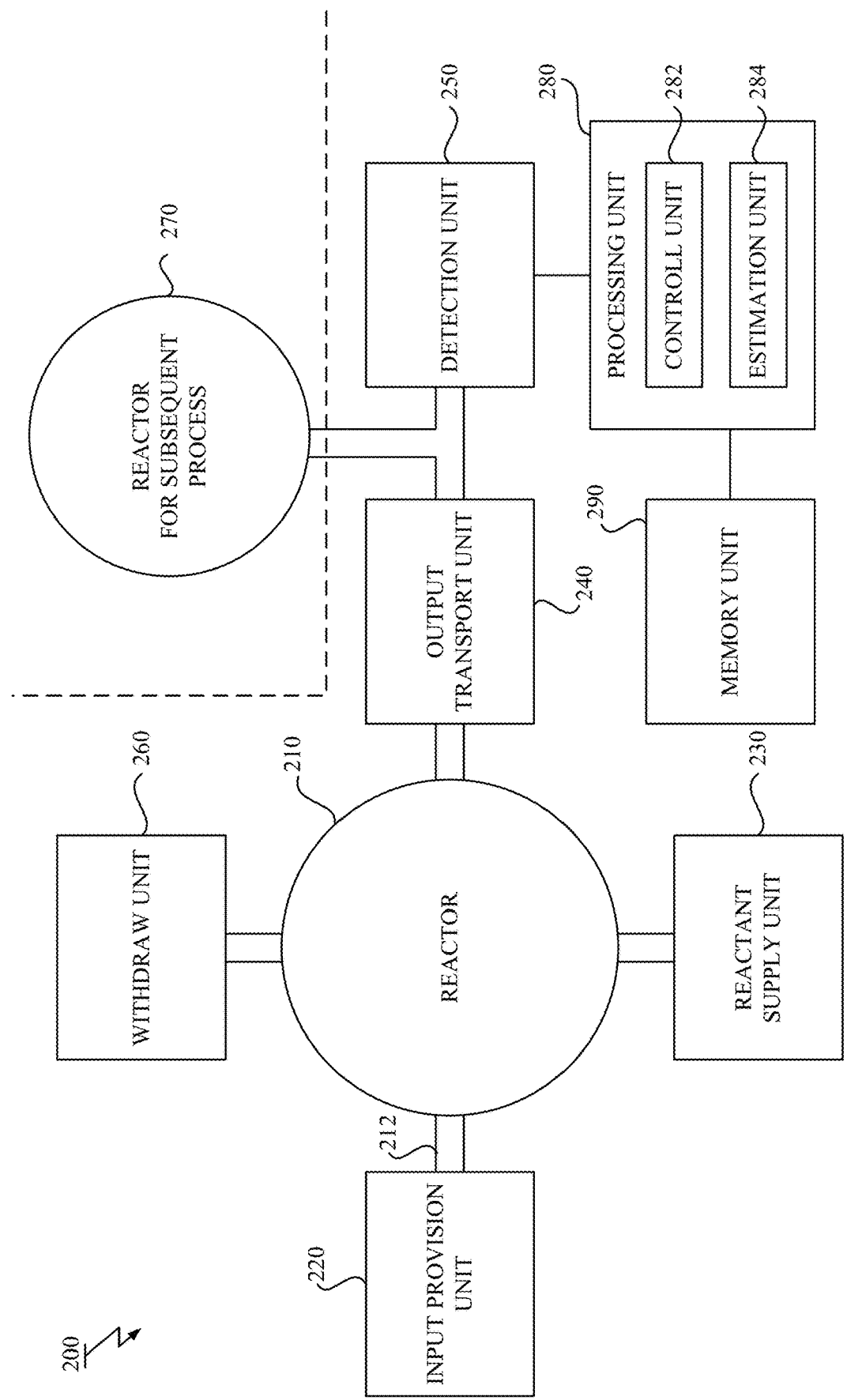
FIG. 13 depicts a schematic of a chemical circuit device implementing the chemical reaction network according to an exemplary embodiment of the present disclosure.

As shown in FIG. 13, the chemical circuit device 200 may include a reactor 210; an input provision unit 220; a reactant supply unit 230; an output transport unit 240; an detection unit 250; a withdraw unit 260; a reactor 270 for subsequent process; a processing unit 280 and a memory unit 290.

The reactor 210 is used to carry out the chemical reactions of the chemical reaction network 150 shown in FIG. 4 or the chemical reaction network 160 shown in FIG. 10. The reactor 210 retains the solution containing the reactants. The reactor 210 may be a closed system where a finite initial supply of reactants is provided and all reactions are finished. In other embodiment, the reactor 210 may be a droplet that is manipulated by a set of electrodes by way of the technique of the digital microfluidics (DMF). In further other embodiment, the reactor 210 may be a continuous flow system where fresh reactants are provided and the waste are withdrawn continuously. The chemical reactions in the reactor 210 may be performed homogeneously.

The input provision unit 220 is configured to provide the solution containing the input chemical species I ($O_0$) with a certain concentration [I]. The input provision unit 220 may include a reservoir for retaining the solution of the input chemical species with the concentration [I] and a device for moving the solution between the reservoir and the reactor 210 through a flow channel or tube 212. Examples of the device used for the input provision unit 220 includes an actuator such as a pump, a gravity-driven infusion device, a digital microfluidic device, and the like. In a particular embodiment, the input provision unit 220 is configured to transport the solution containing the input chemical species I ($O_0$) from a reactor for previous process to the reactor 210 for the current function.

The reactant supply unit 230 is configured to provide solution containing reactants, including a set of gate species (e.eg. $G_0$~$G_4$) and a set of auxiliary species. The reactant supply unit 230 may include a reservoir for retaining the solution of the reactants and a device for moving the solution between the reservoir and the reactor 210 through a flow channel or tube. Examples of the device used for the reactant supply unit 230 includes an actuator such as a pump, a gravity-driven infusion device, a digital microfluidic device, and the like.

The output transport unit 240 is configured to transport at least a part of resultant solution in the reactor 210, which may contain the pattern of the output chemical species (e.g. $O_1$~$O_5$), to the detection unit 250 or the reactor 270 for the subsequent process depending on the function requested. The output transport unit 240 may include a device for moving the solution between the reactor 210 and the detection unit 250 or the reactor 270 for the subsequent process through a flow channel or tube. Examples of the device used for the output transport unit 240 includes an actuator such as a pump, a gravity-driven infusion device, a digital microfluidic device, and the like.

The detection unit 250 is configured to detect at least presence of each of the plurality of output chemical species to identify the pattern. The detection unit 250 includes the set of detectors 120-1~120~N shown in FIG. 1. The detection unit 250 is based on one technique selected from the group consisting of a polymerase chain reaction (PCR) method, a DNA microarray, a RNA sequencing method, a surface plasmon resonance (SPR) sensor, a nanopore method, an electrochemical sensor and a colorimetric sensor.

The PCR method is a method for amplifying a specific DNA sample to a large enough amount. The DNA microarray is based on the hybridization of RNA with complementary probes prefabricated in a plurality of spots on microarray platform. The RNA sequencing method is a method where the complementary DNA library is prepared from target RNAs and massively parallel sequencing of the library derived cDNA are performed. The SPR sensor is based on the measurement of refractive index changes resulting from the surface immobilized molecular interaction between RNAs and the bioreceptor. The nanopore method is based on the principle that the charge transport in the nanopore is halted in the presence of RNA target of interest and the resultant blockade current can be quantified as a signal indicating the presence of the target RNA.

There are several types of the electrochemical devices for detection of the nucleic acid. An electrochemical sensor of first type uses cisplatin-biotin labeled mRNA/redox polymer bilayer formed on a gold electrode. Enzymatic oxidation of glucose oxidase-avidin molecules produce detectable amperometric signal. An electrochemical sensor of second type uses target fusion messenger RNA induced conformational change of the hairpin prove that results in a readable electrochemical signal. An electrochemical sensor of third type uses target fusion messenger RNA captured on amino acid/nucleic acid chimeras capture probe functionalized gold microelectrodes. Voltammetric reading enables the detection in the presence of a complex $[Ru(NH_3)_6]^{3+}/[Fe(CN)_6]^{3-}$. An electrochemical sensor of fourth type uses direct adsorption of magnetically captured target fusion RNAs on the unmodified screen-printed gold electrodes via RNA-gold affinity interaction. Resultant coulombic repulsion between negatively charged RNA and ferricyanide ions produces detectable voltammetric signal.

The colorimetric sensor is a sensor for visual judgement based on a mechanism where a color changes when the sensor comes into contact with a target molecule. The color change may be detected by visually or using an appropriate image sensor. The colorimetric sensor is cost effective among the aforementioned methods.

The withdraw unit 260 is configured to withdraw at least a part of resultant solution including the waste from the reactor 210. The withdraw unit 260 may include a tank for storing a collected solution including the waste and a device for moving the solution between the reactor 210 and the tank through a flow channel or tube. Examples of the device used for the withdraw unit 260 includes an actuator such as a pump, a digital microfluidic device, and the like. The withdraw unit 260 can reset the reactor for the estimation of the next cycle.

The processing unit 280 may be any one of an electronic processor, an electronic circuit device, CPU (Central Processing Unit), FPGA (Field Programmable Gate Array), etc. The processing unit 280 includes a control unit 292 configured to expose the input solution to the chemical reaction network by controlling a valve or a separator disposed in the flow channel or tube 212 between the input provision unit and the reactor 210.

The processing unit 280 further include an estimation unit 294 configured to estimate a concentration range to which the concentration of the input chemical species falls according to detected result of the pattern of the output chemical species. The pattern indicates a dominant species among the plurality of output chemical species as a result of progress of the chemical reaction network 150 shown in FIG. 4 or the chemical reaction network 160 shown in FIG. 10.

The memory unit 290 is operably coupled to the processing unit 280 and is configured to store the calibration parameters that represents the relationship between the predetermined patterns and the predetermined ranges of concentration of the input chemical species. The calibration parameters stored in the memory unit 290 may be read by the processing unit 280 to estimate the concentration range.

The chemical circuit device shown in FIG. 13 can perform a function by utilizing chemical reactions. In a particular embodiment, the function is readout of the concentration of the input chemical species. In other particular embodiment, the function is supply of output chemical species to a subsequent process depending on the concentration of the input chemical species.

Note that the chemical circuit device shown in FIG. 13 is implemented by combining the chemical circuit and the hardware devices such as electronic units, mechanical units, etc. However, in other embodiments, a chemical circuit device can be implemented by using artificial cell membranes as a reactor. Also, implementing the chemical circuit device in the living cells as molecular devices is not hindered.

Figure 14:
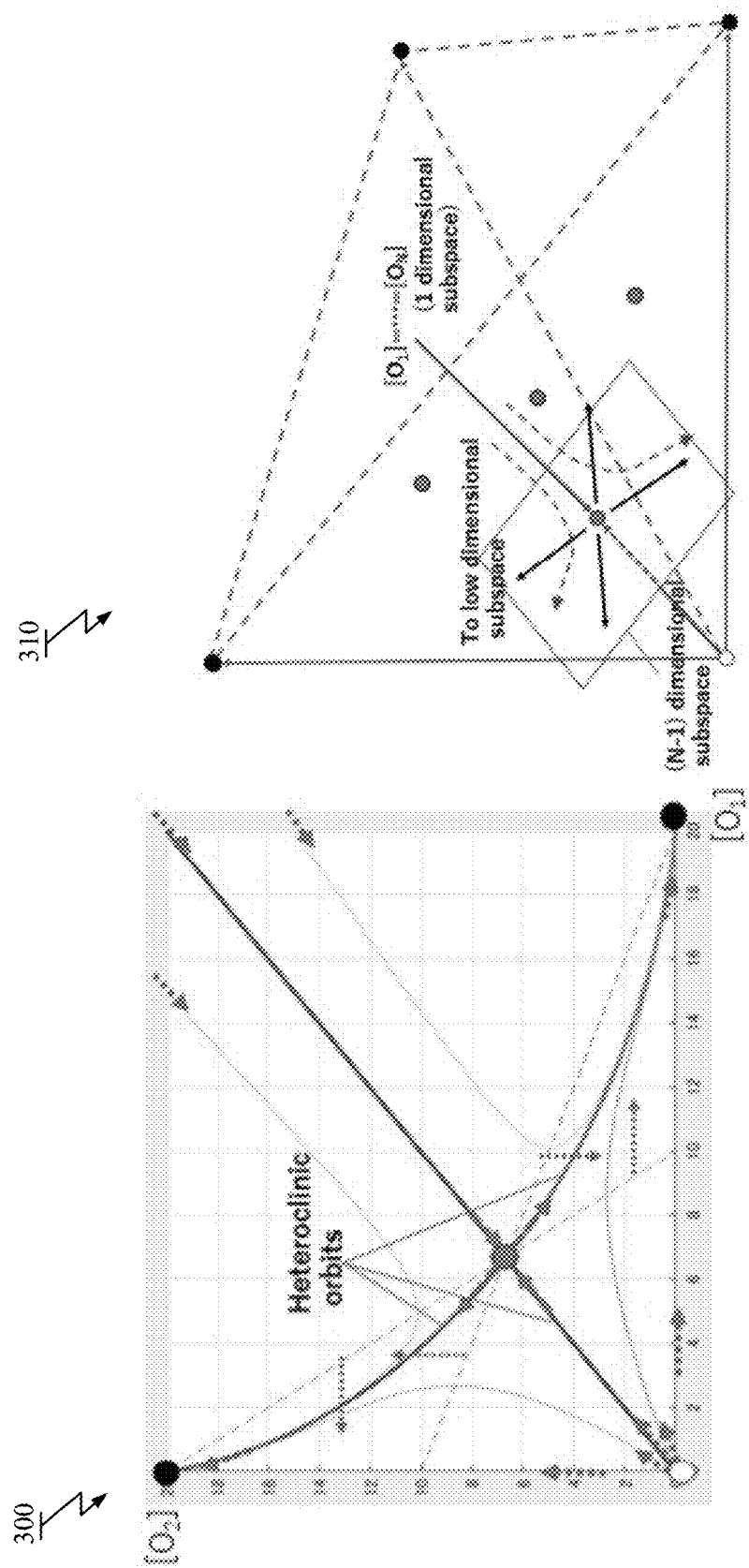
FIG. 14 shows a phase portrait of a 2-species consensus network and a local picture of behavior around a fixed point located inner of the hyper tetrahedron in an extended N-species consensus network.
Figure 15:
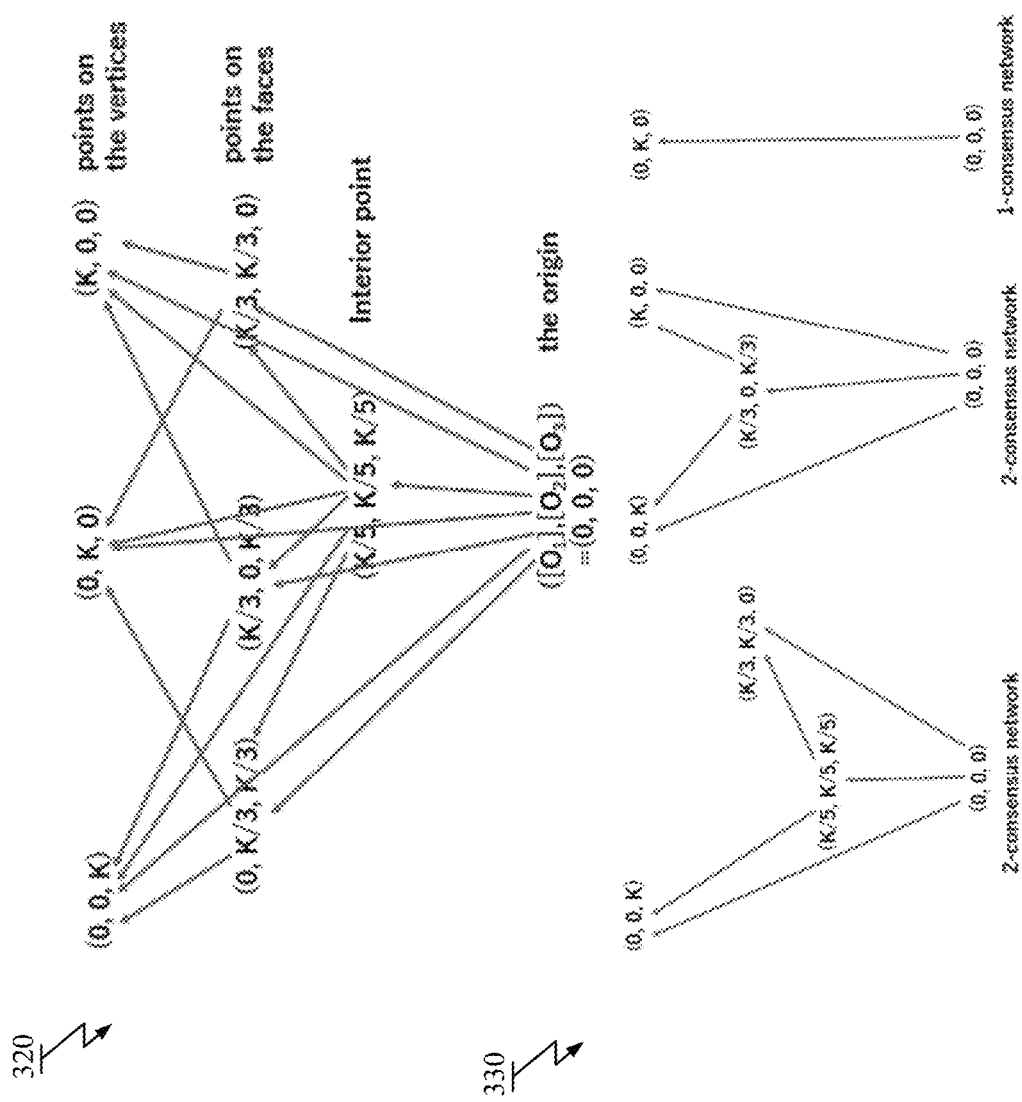
FIG. 15 shows fixed points and heteroclinic orbits of a 3-species consensus network and sub-consensus networks embedded in the consensus network.
Figure 16:
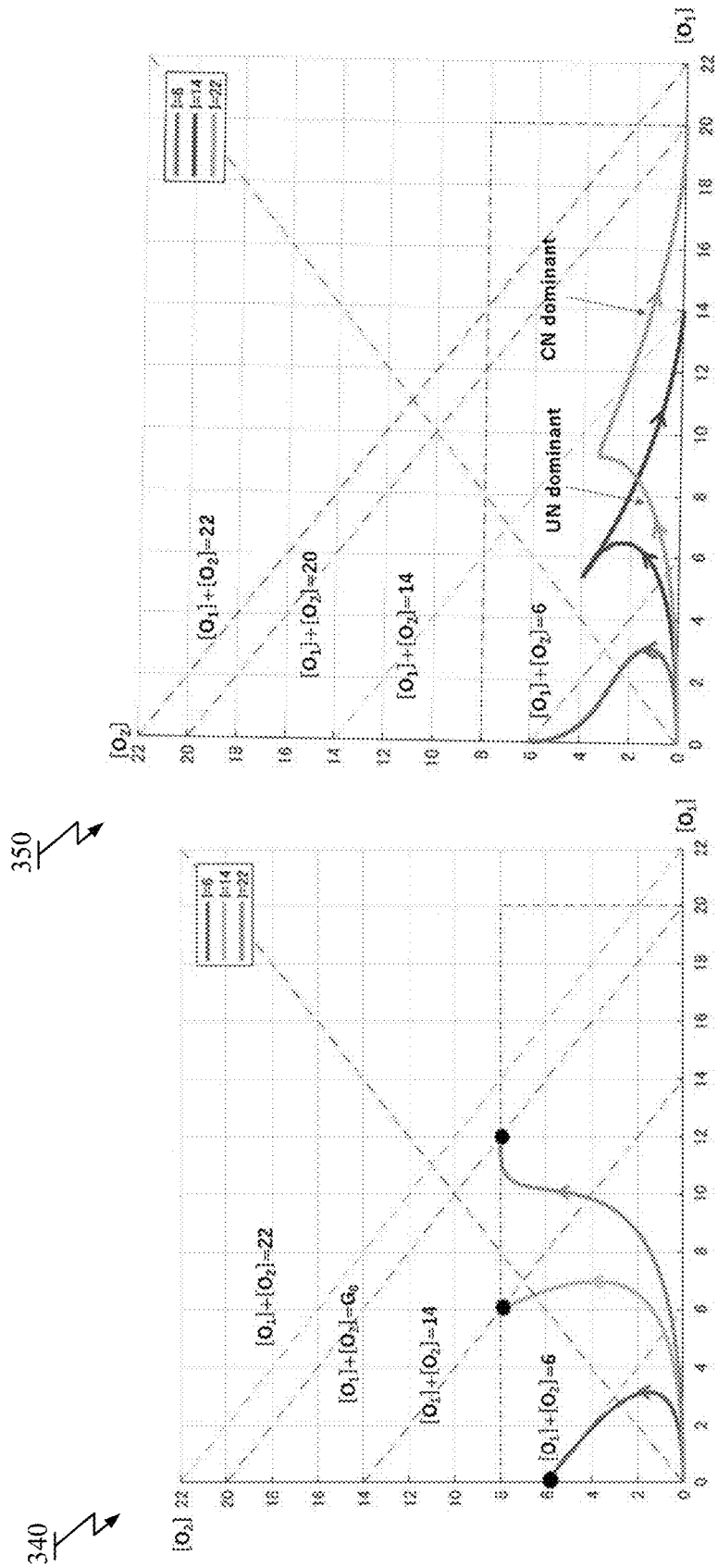
FIG. 16 shows phase portraits of the up-converters (only UC) and a combination of a consensus network (CN) and the up-converters (UC).

With reference to a series of FIGS. 14-16, a geometrical analysis of the chemical reaction network composed of the consensus network and up-converters shown in FIG. 4 is further described.

The geometrical analysis provides insight how consensus network and up-conversion network can operate as an estimator of the concentration of the input chemical species from viewpoint of the geometrical theory of the nonlinear dynamical systems.

The geometrical qualitative analysis would provide us with useful insight into the behavior of the systems. Now let us start with the 2-species consensus network given by following differential equations:

$$\frac{d[O_1]}{dt} = [O_1][X] - [O_1][O_2], \quad (6)$$

$$\frac{d[O_2]}{dt} = [O_2][X] - [O_1][O_2], \quad (7)$$

$$\frac{d[X]}{dt} = [O_1][O_2] - [O_1][X] - [O_2][X]. \quad (8)$$

Note that the reaction rate constants is set to be 1 for simplicity. Though the system involves three variables, the variable [X] can be eliminated and the system can be reduced to a two dimensional system by using the law of mass conservation $[O_1]+[O_2]+[X]=K$ as follows:

$$\frac{d[O_1]}{dt} = [O_1](K - [O_1] - 2[O_2]), \quad (9)$$

$$\frac{d[O_2]}{dt} = [O_2](K - 2[O_1] - [O_2]). \quad (10)$$

There are four fixed points in the reduced system; $([O_1], [O_2])=(0, 0), (0,K), (K, 0), (K/3, K/3)$. The eigenvalue analysis at these four fixed points shows that the two fixed points $(0,K)$ and $(K, 0)$ are stable, and the origin $(0,0)$ is unstable. Also, the fixed point $([O_1], [O_2])=(K/3,K/3)$ is the saddle type since the eigenvalues of the Jacobian at $(K/3, K/3)$ are $-K/3, K/3$, one positive and one negative, and the corresponding eigenvectors are $(1,1)$ and $(-1,1)$, which are orthogonal to each other.

In addition to the eigenvalue analysis, nullclines help us understand the dynamics of the nonlinear systems. A nullcline of a variable is defined as a set of points in the phase space on which the derivative of the variable vanishes (dx/dt=0 where x denotes the variable). When an orbit goes across a nullcline, the sign of the derivative of the variable for the nullcline changes and therefore the nullclines tell us a rough picture of the system behavior. In the exemplary case, the nullclines are composed of the following four straight lines:

$[O_1]=0$ and $[O_1]+2[O_2]=K$ for $[O_1]$, and $[O_2]=0$ and $2[O_1]+[O_2]=K$ for $[O_2]$.

FIG. 14 shows a phase portrait 300 of 2-species consensus network, where K=20. The dashed lines and the axes correspond to nullclines. The dashed arrows indicates the vector field on the nullclines.

The line $[O_1]=[O_2]$ separates the phase space into two regions, and it can be seen that the system can operate as a consensus network. The remarkable feature of the system is that the existence of the orbits connecting two fixed point with two different properties (i.e., the saddle and stable/unstable fixed points), each of which is called a heteroclinic orbit. The existence of the heteroclinic orbits characterizes the overall structure of the consensus network. This geometric analysis can be extended to the following consensus networks with N species as follows:

$$\frac{d[O_i]}{dt} = [O_i]\left([X] - \sum_{j \neq i}[O_j]\right), \quad (11)$$

$$\frac{d[X]}{dt} = 2\sum_{i,j,j\neq i}[O_i][O_j] - [X]\sum_{i}[O_i]. \quad (12)$$

Similar to the two-species case, using the law of mass conservation, $[O_1]+ \ldots +[O_N]+[X]=K$, the system can be reduced to the system as follows:

$$\frac{d[O_i]}{dt} = [O_1]\left(K - [O_1] - 2\sum_{j \neq i}[O_j]\right). \tag{13}$$

The phase space of the consensus network with N species is a hyper tetrahedron in N dimensional Euclidean space, $[O_i] \geq 0$, $[O_1] + \ldots + [O_N] = \leq K$. There are two choices of the nullclines for each the output chemical species $[O_i]$ and therefore there are $2^N$ fixed points in the N-species consensus network. The dynamics of the multi-species consensus network is characterized by the $2^N$ fixed points on the faces and the vertices of the hyper tetrahedron and the heteroclinic orbits connecting them. The fixed point located inner of the hyper tetrahedron is $[O_1] = \ldots = [O_N] = K/(2N-1)$. The Jacobian at this fixed point is the circulant matrix generated by N dimensional vector $K/(2N-1)(N-2, -1, \ldots, -1)$. From the general theory of the circulant matrices, it can be seen that it has only one negative eigenvalue $-K/(2N-1)$ with the eigenvector $(1, \ldots, 1)$ and the other eigenvalues are all $K(N-1)/(2N-1) > 0$.

FIG. 14 also depict a diagram 310 showing $2^N$ fixed points and the local picture of behavior around the fixed point $[O_1] = \ldots = [O_N] = K/(2N-1)$, where the white circle represents the origin, the black circle represents the stable points on the vertices, the gray circle denotes the saddle points on the faces. The orbits move along the 1-dimensional stable subspace and then separated by the N−1 dimensional unstable subspace depending on the relative magnitude of $[O_i]$'s and lead to the low dimensional subspace along the heteroclinic orbits.

The diagram 320 of FIG. 15 shows fixed points and heteroclinic orbits connecting them in a 3-species consensus network. Note that a multi-species consensus network naturally contains many sub-consensus networks with fewer species including the trivial consensus network with only one species $[O_i] \rightarrow K$ ('→' denotes allow of a limit) as shown the diagram 330 of FIG. 15. This is because the multi-species consensus network reduces to smaller ones if some of the variables are set to be equal to zero as $[O_i] = [O_j] = \ldots = [O_k] = 0$ or some variables are set to be equal to each other as $[O_i] = [O_j] = \ldots = [O_k]$. The overall dynamics of the consensus network follows one of heteroclinic orbits depending on its initial state and is attracted to lower dimensional subspace. Then, the dynamics again follows another heteroclinic orbit of the lower dimensional consensus network embedded in that subspace, and finally reaches one of the stable fixed points on the axis. In summary, the structure of the multi-species consensus network can be described by hierarchically organized network of heteroclinic orbits.

Next, the two-species up-conversion network is described by the following differential equations:

$$\frac{d[I]}{dt} = -[I][G_0], \tag{14}$$

$$\frac{d[G_0]}{dt} = -[I][G_0], \tag{15}$$

$$\frac{d[G_1]}{dt} = -[O_1][G_1], \tag{16}$$

$$\frac{d[O_1]}{dt} = [I][G_0] - [O_1][G_1], \tag{17}$$

$$\frac{d[O_2]}{dt} = [O_1][G_1]. \tag{18}$$

Using the mass conservation law, $[O_1]+[O_2]+[G_0]=G_0(:=[G_0](0))$, $[O_1]+[O_2]+[I]=I$ $(:=[I](0))$ and $[O_2]+[G_1]=G_1(:=[G_1](0))$, several variables $[I]$, $[G_0]$ and $[G_1]$ can be eliminated and the following equations are obtained:

$$\frac{d[O_1]}{dt} = (I - [O_1] - [O_2])(G_0 - [O_1] - [O_2]) - [O_1](G_1 - [O_2]), \tag{19}$$

$$\frac{d[O_2]}{dt} = [O_1](G_1 - [O_2]). \tag{20}$$

Introducing a new variable $P = [O_1] + [O_2]$, $dP/dt = (I-P)(G_0-P)$ is obtained. This is a closed form equation only for P, and assuming $G_0 > G_1$, the final state of P, $[O_1]$ and $[O_2]$ can be found as follows:

(a) If $I < G_1$, then $P \rightarrow I$, $[O_1] \rightarrow 0$, $[O_2] \rightarrow I$.

(b) If $G_1 < I < G_0$, then $P \rightarrow I$, $[O_1] \rightarrow I - G_1$, $[O_2] \rightarrow G_1$.

(c) If $I > G_0$, then $P \rightarrow G_0$, $[O_1] \rightarrow G_0 - G_1$, $[O_2] \rightarrow G_1$ The phase portrait 340 of the up-converters is shown in FIG. 16. In the case (a) and (b), the system has a single global fixed point at the intersection of $[O_1]+[O_2]=I$ and the edges of the rectangle. The single global fixed point moves along the edges of the rectangle while I increases from 0 toward $G_0$. On the other hand, in case (c), the single global fixed point stays at $(G_0-G_1, G_1)$. The analysis described here can be extended to the higher dimensional up-converters. The intersection point moves along the edges of the hypercube as the input I increases from zero, and finally stays at a point on an edge when $I > G_0$.

The estimator of the concentration of the input chemical species can be understood as collaboration of the consensus network and up-converters. The two-species estimator involves the following six variables $[I]$, $[G_0]$, $[G_1]$, $[O_1]$, $[O_2]$ and $[X]$. Following the same arguments in the aforementioned analysis, the variable $[G_0]$ and $[X]$ can be eliminated by using the mass conservation laws and the following equations are obtained:

$$\frac{d[I]}{dt} = -[I]([I] + [G_0] - I), \tag{21}$$

$$\frac{d[G_1]}{dt} = -[O_1][G_1], \tag{22}$$

$$\frac{d[O_1]}{dt} = [I]([I] + [G_0] - I) - \tag{23}$$
$$[O_1][G_1] - [O_1][O_2] + [O_1](I - [I] - [O_1] - [2]),$$

$$\frac{d[O_2]}{dt} = [O_2][G_1] - [O_1][O_2] + [O_2](I - [I] - [O_1] - [O_2]), \tag{24}$$

At first, the up-converters dominate the overall dynamics because the initial points are zero on $[O_1]$–$[O_2]$ plane, where the vector field of the consensus network vanishes. After the dynamics of up-converters reach its stable points, the entire dynamics switches to the consensus network having a state where corresponding output chemical species is dominant as a stable fixed point and heteroclinic orbits connecting to the stable fixed point. As has been described in the aforementioned analysis, if I is small and $[I]$ goes to 0, the system reduces to the following consensus network:

$$\frac{d[O_1]}{dt} = [O_1](I - [O_1] - 2[O_2]), \quad (25)$$

$$\frac{d[O_2]}{dt} = [O_2](I - 2[O_1] - [O_2]). \quad (26)$$

On the other hand, if I is large enough and [I] goes to I–$G_0$, the system becomes $$\frac{d[O_1]}{dt} = [O_1](G_0 - [O_1] - 2[O_2]), \quad (27)$$

$$\frac{d[O_2]}{dt} = [O_2](G_0 - 2[O_1] - [O_2]). \quad (28)$$

The phase portrait 350 of a combination of the up-converters and the consensus network is shown in FIG. 16, As shown in the phase portrait 350 of FIG. 16, the final state depends on the state of the system when the switching from up-converters and the consensus network occurs, which explains how the combination of the consensus network and the up-converters work as an estimator of concentration of input chemical species I.

Hereinabove, the methods and the chemical circuit devices according to one or more embodiments of the present disclosure have been described. According to the aforementioned embodiments, a novel technique of classifying a concentration of a chemical species such as nucleic acids into one of classes represented in more accessible forms in a chemical circuit is provided.

The technique according to the embodiment of the present disclosure allows for the classification of the concentration of the input chemical species into the class represented by the pattern of the plurality of output chemical species, which is a more accessible form than the concentration of the input chemical species itself.

In a preferable embodiment where the function is readout of the concentration of the input chemical species, it enables us to read the concentration of the input chemical species in a more readable form than the concentration of the input chemical species itself, which is generally an analog value of a single variable. Also, the concentration of the input chemical species can be quantified with high robustness and a low cost. Also, the accuracy of the estimation of the concentration can be improved by combining other existing technique.

In a further preferable embodiment where the pattern indicates a dominant species among the plurality of output chemical species, the pattern represents a digital signal having '1' (dominant) at a digit corresponding to the dominant species. Such digital signal can be easily detected and then used to compute a level of the concentration of the input chemical species. The readout resolution of the concentration can be improved by simply increasing the number of output chemical species.

In other preferable embodiment where calibration parameters are prepared, the estimation accuracy can be improved.

In yet other preferable embodiment where the function is supply of output chemical species depending on the concentration of the input chemical species, the subsequent process can be controlled by the output chemical species that is a function of the concentration of the input chemical species.

In a preferable embodiment where the input and output chemical species are nucleic acid strand having a representative domain and a toehold domain and each reaction in the sequence of chemical reactions includes a cascade of nucleic acid strand displacement reactions, the concentration of the nucleic acid strand, which may relating to a biomarker, can be quantified with high robustness and a low cost. Since the nucleic acid strand displacement reaction is known for a universal, versatile reaction that can implement arbitrary chemical reaction networks, the chemical reaction network can be designed flexibly. Also, the nucleic acid strand displacement reaction does not require an enzyme and the chemical reaction can proceed by simply exposing the input chemical species to the chemical reaction network. Also, each nucleic acid strand displacement reaction can be implemented using merely nucleic acids.

Although the advantages obtained with respect to the one or more specific embodiments according to the present disclosure have been described, it should be understood that some embodiments may not have these potential advantages, and these potential advantages are not necessarily required of all embodiments.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, layers, elements, and/or components, but do not preclude the presence or addition of one or more other features, steps, layers, elements, components, and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more aspects of the present disclosure has been presented for purposes of illustration and description, but is not intended to be exhaustive or limited to the disclosure in the form disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
  providing a solution comprising an input chemical species having a concentration wherein the input chemical species is a nucleic acid strand having a representative domain and a toehold domain;
  preparing a chemical reaction network comprising at least a sequence of chemical reactions starting with the input chemical species to generate a plurality of output chemical species, wherein the plurality of output chemical species are a plurality of unique nucleic acid strands each having a unique representative domain and a toehold domain, wherein each reaction in the sequence of chemical reactions includes a cascade of nucleic acid strand displacement reactions;
  exposing the solution to the chemical reaction network to present a pattern formed by the plurality of output chemical species depending on the concentration of the input chemical species;

identifying the pattern by detecting at least a presence of each of the plurality of output chemical species; and estimating a concentration range in which the concentration of the input chemical species falls according to the pattern of the output chemical species.

2. The method of claim 1, wherein the pattern indicates a dominant species among the plurality of output chemical species as a result of progress of the chemical reaction network.

3. The method of claim 1, wherein the estimating comprises obtaining calibration parameters representing a relationship between predetermined patterns and predetermined ranges of concentration.

4. The method of claim 1, wherein the function is supply of one or more output chemical species depending on the concentration of the input chemical species and the method comprises:

supplying at least a part of resultant solution containing the pattern of the output chemical species to a subsequent process.

5. The method of claim 1, wherein the sequence of chemical reactions comprises a first set of linked chemical reactions each converting a lower one of the output chemical species into an upper one of the output chemical species, starting from the input chemical species as a lowermost.

6. The method of claim 5, wherein the first set of linked chemical reactions comprises a set of gate species each being consumed to convert the lower one of the output chemical species into the upper one of the output chemical species, the set of gate species being given at respective initial concentrations decreasing towards an upper side along the first set of linked chemical reactions.

7. The method of claim 1, wherein the chemical reaction network comprises further a second set of chemical reactions for forming consensus among the plurality of output chemical species generated from the sequence of chemical reactions so as to single out major chemical species.

8. The method of claim 7, wherein the second set of chemical reactions comprises first reactions each converting a pair of different output chemical species into a buffer species and second reactions each converting the buffer species into one of the output chemical species using the one of the output chemical species itself.

9. The method of claim 1, wherein the chemical reaction network comprises further a third set of chemical reactions each converting an upper output chemical species into a lower output chemical species, with product sides along the sequence of chemical reactions as upper sides.

10. The method of claim 9, wherein the upper output chemical species is converted into the lower output chemical species using the lower output chemical species itself.

11. The method of claim 1, wherein the cascade of nucleic acid strand displacement reactions comprises auxiliary strands with excess amount so that a bimolecular elementary reaction in the cascade of nucleic acid strand displacement reactions becomes a rate-limiting step.

12. The method of claim 1, wherein a rate constant for the cascade of nucleic acid strand displacement reactions is affected by a number of bases and guanine-cytosine content of toehold domains of a nucleic acid strand involved therein.

13. The method of claim 1, wherein the chemical reaction network has a plurality of states where respective output chemical species are dominant as stable fixed points and has heteroclinic orbits connecting to the stable fixed points.

14. An artificial biological synthetic circuit device comprising:

an input provision unit configured to provide a solution comprising an input chemical species having a concentration, wherein the input chemical species is a nucleic acid strand having a representative domain and a toehold domain;

a reactor used to carry out a chemical reaction network, the chemical reaction network comprising at least a sequence of chemical reactions starting with the input chemical species to generate a plurality of output chemical species, wherein the plurality of output chemical species are a plurality of unique nucleic acid strands each having a unique representative domain and a toehold domain, wherein each reaction in the sequence of chemical reactions includes a cascade of nucleic acid strand displacement reactions;

a control unit configured to expose the solution to the chemical reaction network to present a pattern formed by the plurality of output chemical species depending on the concentration of the input chemical species;

a detection unit configured to detect at least a presence of each of the plurality of output chemical species to identify the pattern; and a processing unit configured to estimate a concentration range in which the concentration of the input chemical species falls according to the pattern of the output chemical species.

15. The chemical circuit device of claim 14, wherein the detection unit is based on one technique selected from the group consisting of a polymerase chain reaction (PCR) method, a DNA microarray, a RNA sequencing method, a surface plasmon resonance (SPR) sensor, a nanopore method, an electrochemical sensor and a colorimetric sensor.

16. The chemical circuit device of claim 14, wherein the pattern indicates a dominant species among the plurality of output chemical species as a result of progress of the chemical reaction network.

17. The chemical circuit device of claim 14, wherein the chemical circuit device further comprises:

a memory unit for storing calibration parameters representing relationship between predetermined patterns and predetermined ranges of concentration, the calibration parameters being used to estimate the concentration range to which the concentration of the input chemical species falls.

18. The chemical circuit device of claim 14, wherein the function is supply of output chemical species depending on the concentration of the input chemical species and the chemical circuit device further comprises:

an output supply unit configured to supply a resultant solution containing the pattern of the output chemical species to a subsequent process.

19. The chemical circuit device of claim 14, wherein the sequence of chemical reactions comprises a first set of linked chemical reactions each converting a lower one of the output chemical species into an upper one of the output chemical species, starting from the input chemical species as a lowermost.

20. The chemical circuit device of claim 14, wherein the chemical reaction network comprises further a second set of chemical reactions for forming consensus among the plurality of output chemical species generated from the sequence of chemical reactions so as to single out major chemical species.

21. The chemical circuit device of claim 14, wherein the chemical reaction network comprises further a third set of chemical reactions each converting an upper output chemical species into a lower output chemical species, with product sides along the sequence of chemical reactions as upper sides.

* * * * *